US006503749B2

(12) United States Patent
Achstetter et al.

(10) Patent No.: US 6,503,749 B2
(45) **Date of Patent: *Jan. 7, 2003**

(54) YEAST STRAINS POSSESSING THE INTERRUPTED ATF2 GENE AND THEIR APPLICATIONS

(75) Inventors: Tilman Achstetter, Oberkirch (DE); Gilles Cauet, Griesheim/Souffel (FR); Eric Degryse, Strasbourg (FR)

(73) Assignee: Aventis Pharma S.A. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/797,239

(22) Filed: Mar. 1, 2001

(65) Prior Publication Data

US 2001/0012630 A1 Aug. 9, 2001

Related U.S. Application Data

(62) Division of application No. 09/243,367, filed on Feb. 1, 1999, now Pat. No. 6,218,139.

(30) Foreign Application Priority Data

Feb. 5, 1998 (FR) ........................................... 98 01329

(51) Int. Cl.$^7$ ........................... C12N 1/14; C12P 21/04; C12P 33/00; C07H 21/02; C07H 21/04

(52) U.S. Cl. ..................... 435/254.2; 435/52; 435/69.9; 435/193; 435/255.1; 435/255.2; 435/254.11; 435/254.21; 435/320.1; 435/483; 536/23.2; 536/23.74

(58) Field of Search ......................... 435/69.9, 52, 471, 435/483, 193, 320.1, 255.1, 254.11, 254.21, 254.2, 255.2; 536/23.2, 23.74

(56) References Cited

PUBLICATIONS

Fujii et al. Journal of Fermentation and bioengineering. 1996. 81: 538–542.*

* cited by examiner

*Primary Examiner*—Carla J. Myers
(74) *Attorney, Agent, or Firm*—Bierman, Muserlian and Lucas

(57) ABSTRACT

A subject of the invention is a modified yeast strain in which the acetyl-CoA pregnenolone acetyltransferase (APAT) activity is eliminated by altering the gene coding for this activity with resultant stabilization of 3β-hydroxysteroids.

1 Claim, 25 Drawing Sheets

Figure 4:
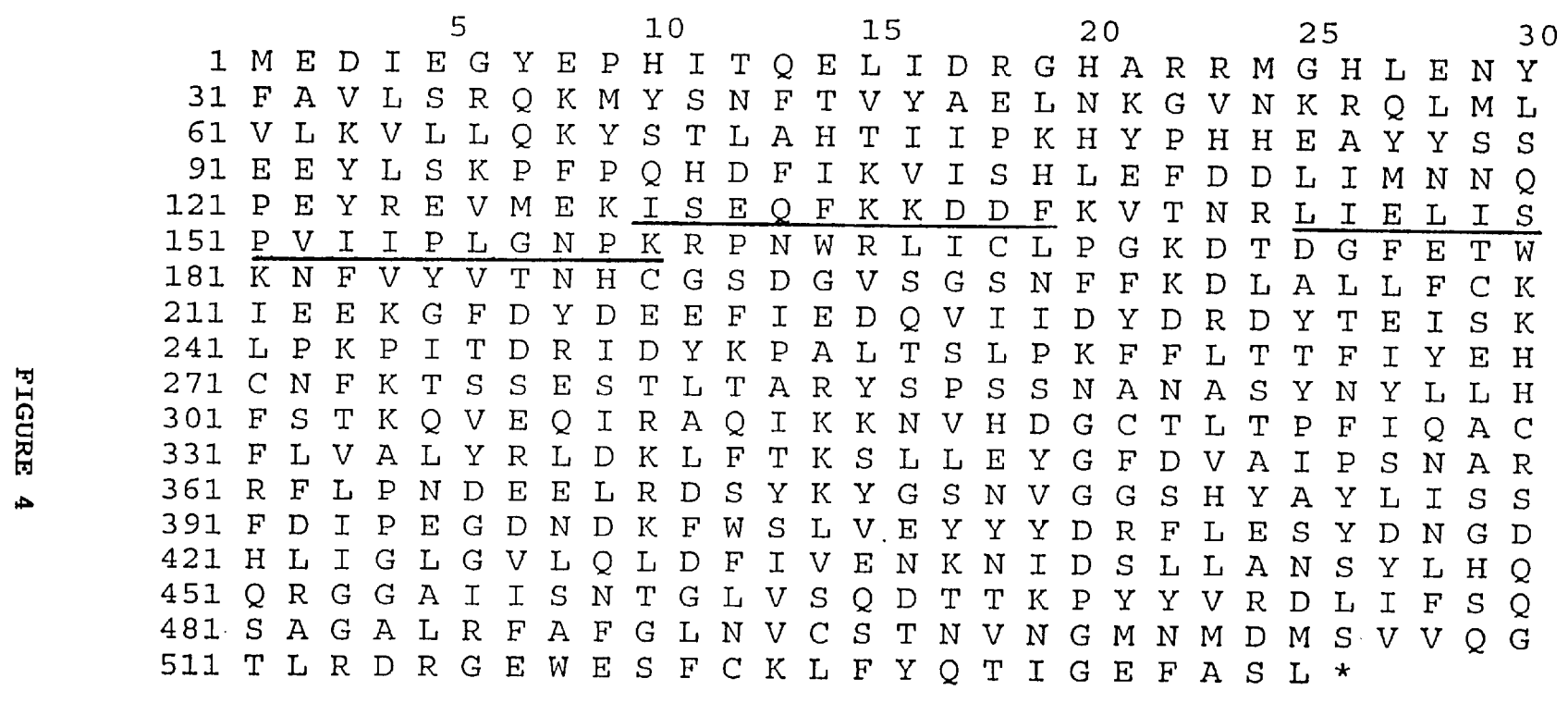

```
                 5         10          15          20          25          30
  1 M E D I E G Y E P H I T Q E L I D R G H A R R M G H L E N Y
 31 F A V L S R Q K M Y S N F T V Y A E L N K G V N K R Q L M L
 61 V L K V L L Q K Y S T L A H T I I P K H Y P H H E A Y Y S S
 91 E E Y L S K P F P Q H D F I K V I S H L E F D D L I M N N Q
121 P E Y R E V M E K I S E Q F K K D D F K V T N R L I E L I S
151 P V I I P L G N P K R P N W R L I C L P G K D T D G F E T W
181 K N F V Y V T N H C G S D G V S G S N F F K D L A L L F C K
211 I E E K G F D Y D E E F I E D Q V I I D Y D R D Y T E I S K
241 L P K P I T D R I D Y K P A L T S L P K F F L T T F I Y E H
271 C N F K T S S E S T L T A R Y S P S S N A N A S Y N Y L L H
301 F S T K Q V E Q I R A Q I K K N V H D G C T L T P F I Q A C
331 F L V A L Y R L D K L F T K S L L E Y G F D V A I P S N A R
361 R F L P N D E E L R D S Y K Y G S N V G G S H Y A Y L I S S
391 F D I P E G D N D K F W S L V E Y Y Y D R F L E S Y D N G D
421 H L I G L G V L Q L D F I V E N K N I D S L L A N S Y L H Q
451 Q R G G A I I S N T G L V S Q D T T K P Y Y V R D L I F S Q
481 S A G A L R F A F G L N V C S T N V N G M N M D M S V V Q G
511 T L R D R G E W E S F C K L F Y Q T I G E F A S L *
```

YEAST STRAINS POSSESSING THE INTERRUPTED ATF2 GENE AND THEIR APPLICATIONS

This application is a division of U.S. patent application Ser. No. 09/243,367 filed Feb. 1, 1999, now U.S. Pat. No. 6,218,139.

The formation of 3-oxo-delta$^4$-steroids from 3β-hydroxy-delta$^5$ precursors in the biosynthesis of all classes of steroid hormones in mammals is catalysed by the enzyme system 3β-hydroxy-delta$^5$-steroid dehydrogenase (EC 1.1.1.145) and delta$^5$-delta$^4$-steroid isomerase (EC 5.3.3.1), designated 3β-HSD. For example, 3β-HSD catalyses the transformation of pregnenolone to progesterone, of 17α-hydroxypregnenolone to 17α-hydroxyprogesterone, of dehydroepiandrosterone to delta$^4$-androstenedione or of 5-androstene-3β-17β-diol to testosterone (Simard et al., 1996).

Thus, 3β-HSD is one of the key enzymes in the route for biosynthesis of hydrocortisone starting from cholesterol in the adrenal cortex of mammals (FIG. 1).

The use of recombinant microorganisms, especially modified yeasts, permitting heterologous expression of one or more of the mammalian enzymes of this biosynthetic route for producing hydrocortisone or intermediates of this biosynthesis was described for example in European patent application EP 340878, U.S. Pat. No. 5,137,822, Dumas et al., 1994 and Cauet et al., 1994.

When functional 3β-HSD is expressed in yeast, the transformed yeast cells do not completely convert 3β-hydroxysteroids to the corresponding 3-oxosteroids, for example pregnenolone to progesterone, but accumulate a compound which is also observed in the case of cells of untransformed yeast. Identification of the compound accumulated as the 3β-acetate ester of the starting steroid and characterization of the enzyme possessing acyltransferase activity which is responsible for this esterification (designated hereinafter as APAT for "acetyl-coenzyme A pregnenolone acetyltransferase") are described in the present application. Furthermore, accumulation of pregnenolone acetate by a pregnenolone-producing transformed yeast strain was described in European patent application EP 727489. It can be considered on the basis of these observations that esterification of the 3β-hydroxysteroids produced by the yeast is undesirable as it is responsible for secondary reactions and by-products leading to a decrease in the yield of accumulated 3β-hydroxysteroids, for example pregnenolone, or to a decrease in the yield of bioconversion of 3β-hydroxy-delta$^5$-steroids to 3-oxo-delta$^4$-steroids, particularly in the production of progesterone or of 17α-hydroxy-progesterone leading to a decrease in subsequent production of hydrocortisone by the biosynthetic route already mentioned.

On the basis of the results obtained, mentioned above, the present invention describes the construction of yeast strains that have lost the undesirable APAT activity, by alteration of the gene coding for this activity, resulting in stabilization of the 3β-hydroxysteroids in the presence of the latter. These strains can therefore be used as starting strains for constructing recombinant strains that are capable of converting 3β-hydroxysteroids to further products with improved yields.

The invention also describes the construction of yeast strains that have lost APAT activity by alteration of the gene coding for this activity and either expressing 3β-HSD or the cytochrome $P_{450}17\alpha$, or co-expressing 3β-HSD and the cytochrome $P_{450}17\alpha$ of the route of biosynthesis of hydrocortisone from cholesterol. The strains expressing for example 3β-HSD make it possible to improve the yields in bioconversion of 3β-hydroxy-delta$^5$-steroids to 3-oxo-delta$^4$-steroids and can therefore be used in processes of improved production of hydrocortisone or of its intermediates in yeast.

A subject of the present invention is therefore a modified yeast strain in which the acetyl-CoA pregnenolone acetyltransferase (APAT) activity is eliminated by altering the gene coding for this activity, resulting in stabilization of the 3β-hydroxysteroids.

Alteration of the gene coding for APAT activity can be effected for example by insertion, deletion or substitution of a DNA sequence in the functional elements of the gene, for example the promoter or the sequence coding for the protein possessing APAT activity. Integration of the DNA sequence altered in this way in a host strain of yeast can then be effected for example by the technique of homologous recombination and leads to the generation of chromosomal mutants of yeast corresponding to the modified strains of the invention in which the disappearance of APAT activity and the stabilization of 3β-hydroxysteroids are demonstrated, for example by cell culture in the presence of pregnenolone and by measuring the pregnenolone content as a function of time, following the operating conditions described later in the experimental section.

The following may be mentioned in particular as host yeast strains used for the invention: strains of Saccharomyces such as *S. cerevisiae*, strains of Candida such as *C. maltosa*, strains of Kluyveromyces such as *K. lactis* or strains of Pichia such as *P. pastoris*.

A particular subject of the invention is a yeast strain modified as above in which the gene altered is the ATF2 gene of *S. cerevisiae* or a homologue of the latter.

By gene ATF2 we mean the gene of *S. cerevisiae* identified in the yeast genome at locus ATF2 or YGR177c, of "Saccharomyces Genome Database" (SGD); (Cherry et al. http://genome-www.stanford.edu/Saccharomyces/) of which the open reading frame (ORF) designated YGR177c is translated into an amino acid sequence in the Mips database, accessible under accession number S64491 (Hebling U., Hofmann B. and Delius H. (May 1996)) and whose sequence is shown in FIG. 4. This gene codes for a protein possessing APAT activity, as is shown later in the experimental section.

By gene that is a homologue of the ATF2 gene, we mean a gene that codes for a protein possessing APAT activity and possessing sequence identity of about 60% or more with the sequence of protein YGR177C.

A more particular subject of the invention is a modified yeast strain as above in which the altered gene is the ATF2 gene of *S. cerevisiae*, designated hereinafter as atf2 mutant strain.

A quite particular subject of the invention is a modified yeast strain as above, in which the ATF2 gene is altered by insertion of a DNA sequence that has at least one nucleotide.

The DNA sequence that is inserted in the ATF2 gene so as to lose all APAT activity can be, for example, an auxotrophic selection gene supplying a nutritional requirement of the host strain such as the gene URA3, the gene LEU2, the gene TRP1, the gene HIS3 or the gene ADE2, for example a dominant selection gene such as a gene for resistance to an antibiotic such as G418, phleomycin or hygromycin B or for example a reporter gene such as the βGAL gene.

The DNA sequence that is inserted in the ATF2 gene can also be a yeast expression block made up of a promoter and a transcription terminator, for example a yeast promoter such as PGK, TDH3, CYC1 or TEF1, for example a yeast terminator such as CYC1, TDH3, TEF1 or PGK. The expression block can be a combination of the elements mentioned above, for example the block $TEF1_{prom}/PGK_{term}$.

A more quite particular subject of the invention is a modified yeast strain as above, in which the ATF2 gene is altered by insertion of the URA3 selection gene or of the expression block $TEF1_{prom}/GK_{term}$.

A particular subject of the invention is a modified yeast strain as above, in which the ATF2 gene is altered by insertion of the URA3 selection gene.

The atf2 mutant strains of the invention, devoid of APAT activity and in which the URA3 gene has been inserted, designated hereinafter as atf2-Δ::URA3, could thus be selected by prototrophy with uracil.

A quite particular subject of the invention is modified strains of *S. cerevisiae* designated as TGY156 and TGY158, the detailed constructions of which are given later in the experimental section.

A particular subject of the invention is also a modified yeast strain as above, in which the ATF2 gene is altered by insertion of the expression block $TEF1_{prom}/PGK_{term}$, The atf2 mutant strains of the invention, devoid of APAT activity and in which the expression block $TEF1_{prom}/PGK_{term}$ has been inserted, designated hereinafter as atf2-Δ::$TEF1_{prom}/PGK_{term}$, could be selected for absence of a functional URA3 gene, replaced by an expression block, by their resistance to 5-fluoro-orotic acid (5-FO).

A quite particular subject of the invention is the modified strain of *S. cerevisiae* designated as TGY186, the detailed construction of which is given later in the experimental section.

A subject of the invention is also a transformed yeast strain in which the acetyl-CoA pregnenolone acetyltransferase (APAT) activity is eliminated by altering the gene coding for this activity and expressing at least one of the mammalian enzymes of the route of biosynthesis of hydrocortisone starting from cholesterol, chosen from:

the cholesterol side chain cleavage enzyme ($P_{450}SCC$),

3β-hydroxy-delta$^5$-steroid dehydrogenase/delta$^5$-delta$^4$-steroid isomerase (3β-HSD) and 17α-steroid hydroxylase ($P_{450}17\alpha$).

The transformed yeast strains of the invention can be obtained for example by transformation of atf2 mutant strains of the invention by known methods, for example by transformation by an expression vector of $P_{450}SCC$ as well as of ADX and ADR, by an expression vector of 3β-HSD or by an expression vector of $P_{450}17\alpha$. The atf2 mutant strains can also be co-transformed if necessary, for example by an expression vector of 3β-HSD and by an expression vector of $P_{450}17\alpha$ or be transformed by a co-expression vector of 3β-HSD and $P_{4450}17\alpha$ and be used for example in a process of bioconversion of pregnenolone to 17α-hydroxyprogesterone.

Vectors constructed for the expression of $P_{450}SCC$ as well as of ADX and ADR, of 3β-HSD or of $P_{450}17\alpha$ of bovine or human origin in yeast strains were described for example by Dumas et al., 1994, in European patent application EP 340878 or in U.S. Pat. No. 5,137,822.

A particular subject of the invention is a transformed yeast strain as above, in which the altered gene is the ATF2 gene of *S. cerevisiae* or a homologue of the latter. A more particular subject of the invention is a transformed yeast strain as above, in which the altered geneis, the ATF2 gene of *S. cerevisiae* and corresponds to a transformed atf2 strain.

A quite particular subject of the invention is a transformed yeast strain as above, in which the ATF2 gene is altered by insertion of a DNA sequence possessing at least one nucleotide and especially a transformed yeast strain in which the ATF2 gene is altered by insertion of the URA3 selection gene and corresponds to a modified atf2-Δ::URA3 strain.

Alteration of the gene so as to lose all APAT activity, the ATF2 gene or a homologue of the latter as well as the host strains have the meanings indicated previously.

A quite particular subject of the invention is a transformed yeast strain atf2-Δ::URA3 as above expressing 3β-HSD and in particular the transformed strain of *S. cerevisiae* designated TGY158/pTG10862 of which a detailed construction is described later in the experimental section.

A quite particular subject of the is also a transformed yeast strain as above, in which the ATF2 gene is altered by insertion of the expression block $TEF1_{prom}/PGK_{term}$ and corresponding to a transformed strain atf2-Δ::$TEF1_{prom}/PGK_{term}$.

A quite particular subject of the invention is also a transformed strain atf2-Δ::$TEF1_{prom}/PGK_{term}$ as above expressing $P_{450}17\alpha$ and in particular the transformed strain of *S. cerevisiae* designated TGY186/pTG10435.

A particular subject of the invention is a modified yeast strain atf2-Δ::$TEF1_{prom}/PGK_{term}$ as above co-expressing 3β-HSD and $P_{450}17\alpha$ and quite particularly the transformed strain of *S. cerevisiae* designated as TGY186/pTG10417.

A subject of the invention is also a process of oxidation in vivo of a substrate chosen among an endogenous sterol, an exogenous sterol or an exogenous steroid in which transformed yeast strain as above is used, which is either cultivated alone when the strain produces the endogenous sterol, or is incubated with the sterol or the exogenous steroid and the oxidized compound obtained is isolated if required.

By endogenous sterol we mean a sterol that is accumulated in a yeast strain and which is a substrate of the side chain cleavage enzyme ($P_{450}SCC$) when the yeast, after transformation for example by an expression vector of $P_{450}SCC$, of ADX and of ADR, is cultivated in the absence of exogenous sterol. The endogenous sterols used for applying the process of the invention can be for example ergosta-5-en-3-ol, ergosta-5,24(28)-dien-3-ol or ergosta-5,22-dien-3-ol. European patent application EP 727489 describes the accumulation of these sterols in a yeast strain and the cleavage of their side chain in a culture of the strain after transformation by an expression vector of $P_{450}SCC$, of ADX and of ADR. Such a yeast strain, in which APAT activity is also present, can be modified beforehand to obtain an atf2 mutant strain according to the invention, then be transformed by an expression vector of $P_{450}SCC$, of ADX and of ADR to obtain an atf2 mutant strain transformed according to the invention.

By exogenous sterol we mean a sterol which is a substrate of the $P_{450}SCC$ cleavage enzyme by incubation with a yeast strain transformed by an expression vector of $P_{450}SCC$, of ADX and of ADR, for example cholesterol or sitosterol. Such a strain can be, for example, an atf2 mutant strain transformed by an expression vector of $P_{450}SCC$, of ADX and of ADR.

The 3β-hydroxysteroid obtained by cleavage of the side chain of the endogenous or exogenous sterol used as substrate is completely in the free form, i.e. is not accompanied by the corresponding 3β-acetate ester, in cultures of transformed atf2 strains expressing $P_{450}SCC$, ADX and ADR.

By steroid we mean a steroid which is a substrate of the 3β-HSD enzyme by incubation with a yeast strain transformed for example by an expression vector of 3β-HSD, such as pregnenolone, 17α-hydroxypregnenolone or dehydroepiandrosterone or a steroid which is a substrate of the $P_{450}17\alpha$ enzyme by incubation with a yeast strain transformed for example by an expression vector of $P_{450}17\alpha$, such as progesterone or pregnenolone. Such a strain can, for example, be an atf2mutant strain transformed by an expression vector of 3β-HSD or by an expression vector of $P_{450}17\alpha$ according to the invention.

A particular subject of the invention is the in-vivo oxidation process as above, in which the substrate is a 3β-hydroxysteroid and in which a transformed yeast strain atf2Δ::URA3 is used, expressing 3β-HSD, and the 3-oxo-delta$^4$-steroid obtained is isolated if necessary, and especially a process in which the 3β-hydroxysteroid is chosen from pregnenolone or 17α-hydroxypregnenolone.

The 3β-hydroxysteroid used as substrate is stable when it is incubated with an atf2-Δ::URA3 strain of the invention, transformed by an expression vector of 3β-HSD. The invention thus provides an improved process for production of 3-oxo-delta$^4$-steroid in a yeast since all of the 3β-hydroxy substrate can be oxidized to 3-oxo-delta$^4$-steroid, as is shown later in the experimental section.

A particular subject of the invention is also the in-vivo oxidation process as above, in which the substrate is a steroid and in which a transformed yeast strain atf2-Δ::$TEF1_{prom}$/$PGK_{term}$ expressing $P_{405}17\alpha$ is used, and the 17α-hydroxyl steroid obtained is isolated if necessary, and especially a process in which the steroid substrate is pregnenolone or progesterone.

The pregnenolone used as substrate is stable when it is incubated with a strain atf2-Δ::$TEF1_{prom}$/$PGK_{term}$ transformed by an expression vector of $P_{450}17\alpha$. The invention thus also provides an improved method of production of 17α-hydroxysteroids starting from 3β-hydroxysteroids since all of the 3β-hydroxy substrate can be 17α-hydroxylated.

A particular subject of the invention is also the above in-vivo oxidation process, in which the substrate is a 3β-hydroxysteroid and in which a transformed yeast strain atf2-Δ::$TEF1_{prom}$/$PGK_{term}$ co-expressing 3β-HSD and $P_{450}$-17α is used, and the 17α-hydroxyl 3-oxo-delta$^4$-steroid obtained is isolated if necessary. A quite particular subject of the invention is the above process in which the steroid substrate is pregnenolone.

The transformed atf2 mutant yeast strains and the process of the invention suggest their advantageous use in improved production of hydrocortisone or of its intermediates in yeast.

Examples of construction of the strains of the invention and of application of the process of the invention are described later in the experimental section.

General Materials and Methods

1. Strains and Media

The strains of *S. cerevisiae* used for carrying out the invention are the strain TGY73.4 (MATα, URA3-Δ5, pral-1, prbl-1, prcl-1, cpsl-3, his) isogenic derivative $Leu^+$ of cl3ABYS86 described by Achstetter et al., 1992 and the strain Fyl679 (MATa, URA3-52, trp1-Δ63, leu2-Δ1, his3-Δ200, fen1, GAL) described by Thierry et al., 1990. The strains are grown on YPD complete medium (Difco Laboratories) containing 2% of glucose at 28° C. according to the conditions described by F. Sherman, 1991.

For the transformation of *S. cerevisiae*, the cells are made competent by the lithium acetate method (Ito et al., 1983). The yeasts are cultivated routinely on a synthetic minimum medium SD containing 2% of glucose (F. Sherman, 1991) with addition of the required nutrients at a concentration of 100 μg/ml.

The *E. coli* strain BJS183 (D. Hanahan, 1983) was used for in-vivo recombination and the *E. coli* strain C600, hsdR (Hubacek et al., 1970) was used as the receiving strain for the classical reactions of ligation.

2. Manipulation of the DNA and Recombination in vivo in *E. coli*

The general methods of molecular biology used are described by Sambrook et al., 1989. The method for recombination in vivo was described by E. Degryse, 1995 and E. Degryse, 1996.

3. Test of APAT Enzyme Activity

The APAT acetyltransferase activity was determined by measuring the incorporation of [$^3$H]acetate in the pregnenolone from [$^3$H]acetyl-CoA (New England Nuclear). The reaction medium (500 μl) contains [$^3$H]acetyl-CoA (20 μM, 25 Ci/mol) and pregnenolone (Sigma) (30 μM). The pregnenolone is added in solution in 2 μl of tyloxapol (Sigma)/ethanol mixture (1:1) in a potassium phosphate buffer (20 mM) at pH 7.0. After incubation for 15 minutes at 30° C., the reaction is stopped by adding 2 ml of dichloromethane.

The steroids are extracted with dichloromethane, then separated by reversed-phase high-performance liquid chromatography (hereinafter: RP-HPLC) in isocratic elution conditions with acetonitrile in an Ultrasphere ODS column (Beckman) at 45° C. on an HP 1090 chromatograph (Hewlett-Packard) connected to a FLO-One 500 radiodetector (Packard) which permits measurement of the amount of pregnenolone [$^3$H]acetate formed.

One APAT unit is defined as the quantity of enzyme that produces 1 nmol of pregnenolone acetate per minute at 30° C., in the conditions described above.

4. Determination of the Concentration of Protein

The protein concentration was measured using the "protein assay kit" (Bio-Rad) with bovine serum albumin as standard.

Some aspects of the invention are illustrated by the figures that are appended.

FIG. 1 shows the route for biosynthesis of hydrocortisone from cholesterol, in mammals.

FIGS. 2A and 2B show the bioconversion of pregnenolone to pregnenolone acetate in *S. cerevisiae*. Analysis is effected by RP-HPLC at 205 nm: FIG. 2A shows the kinetics of formation of pregnenolone acetate and of disappearance of pregnenolone at intervals of time in 12 h of incubation. FIG. 2B shows the steroids profile at t=0 and at t=10 h relative to a profile of pregnenolone and pregnenolone acetate standards.

FIG. 3 illustrates the purification of APAT by chromatography on MonoP HR 5/20:

(A) shows the profile of APAT activity present in fractions 10 to 20.

(B) shows SDS-PAGE analysis of fractions 14, 15 and 16 combined and concentrated by staining with Coomassie blue (line 2) in the presence of molecular weight markers (line 1). The arrow indicates the band of apparent MW of 62 kDa.

FIG. 4 shows the amino acid sequence in single-letter code of protein YGR177c (SEQ ID NO:20). The peptides sequenced on the basis of the APAT protein purified and digested by trypsin are underlined.

Figure 7A:
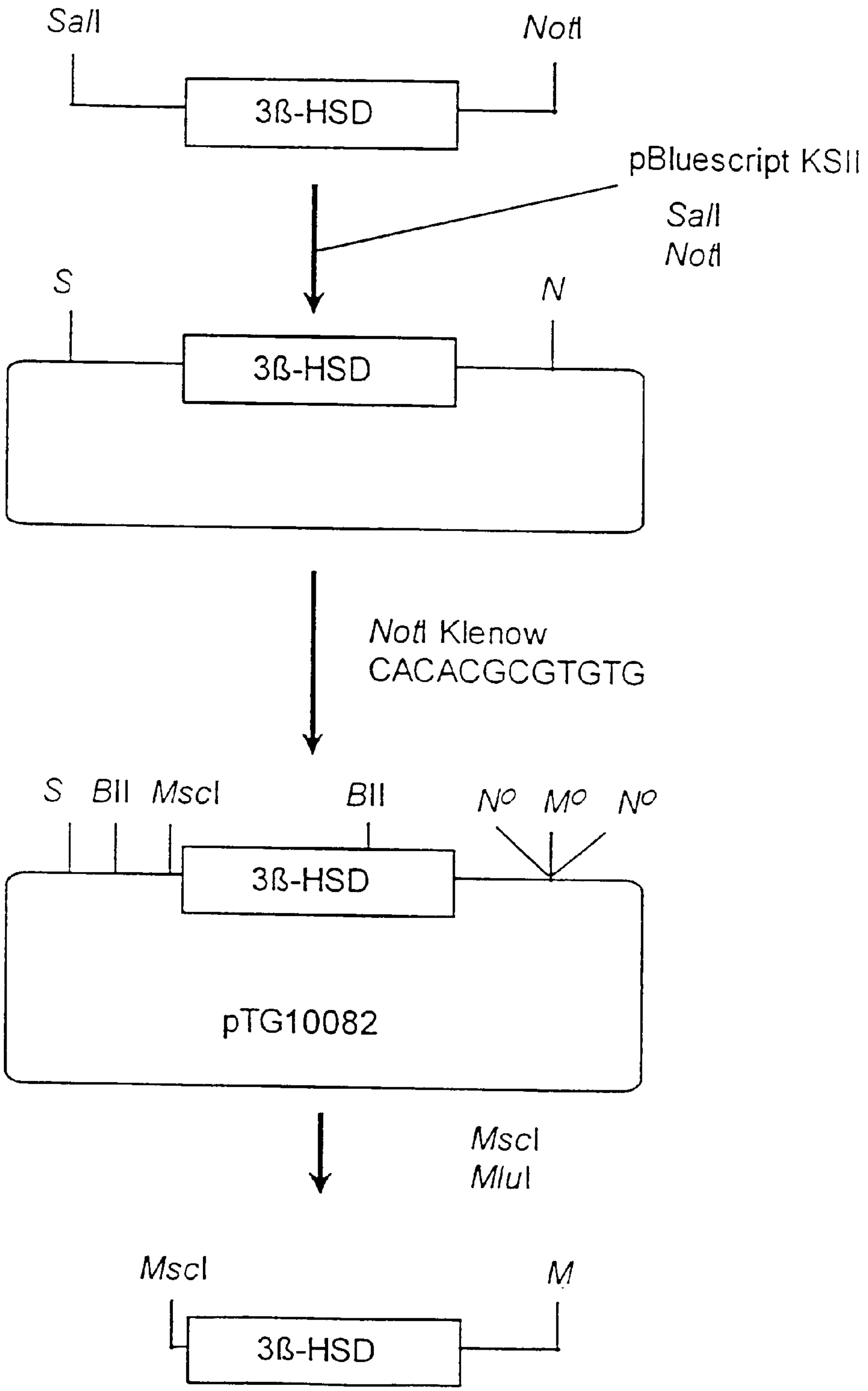
Figure 7B:
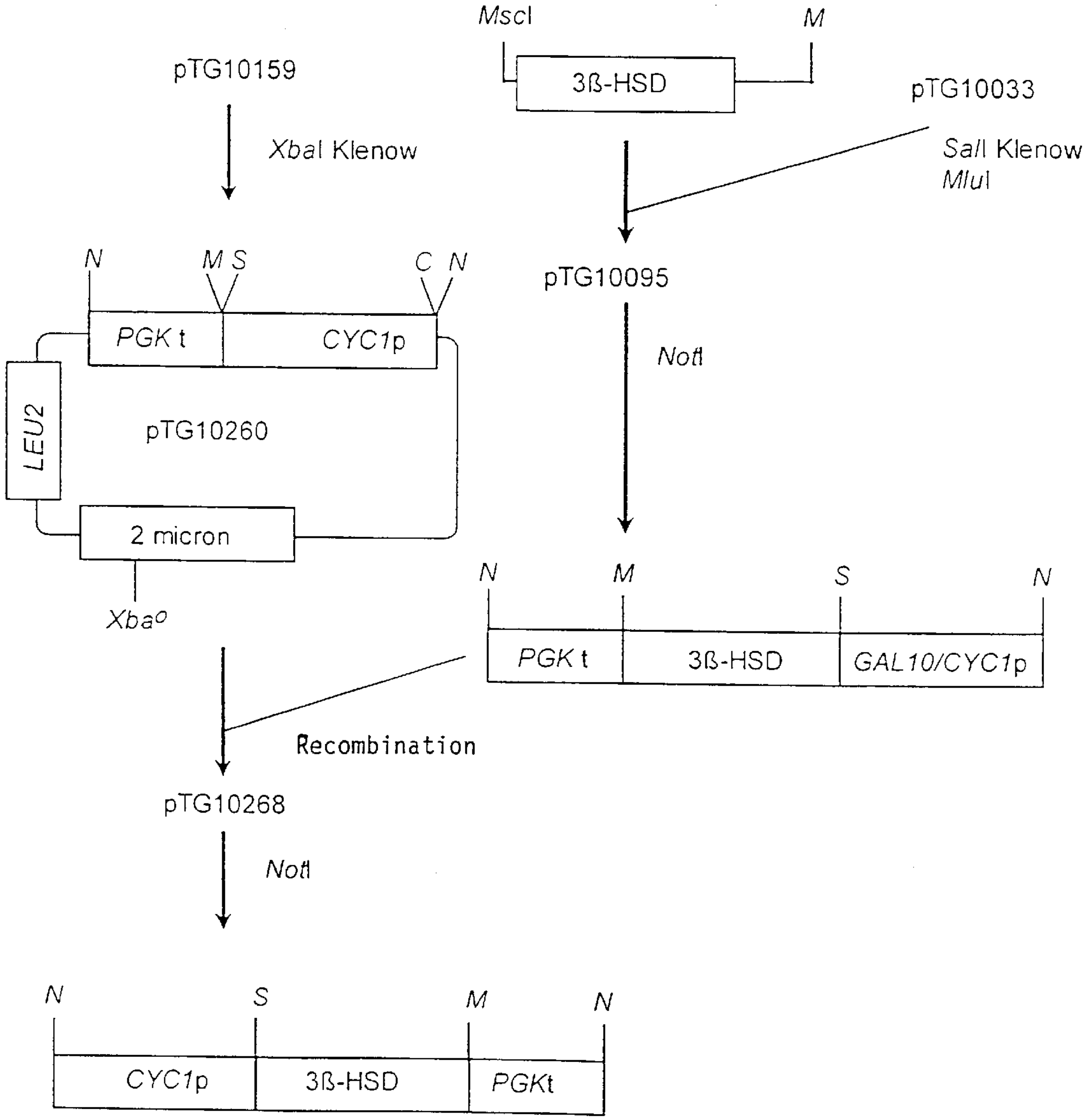
Figure 7C:
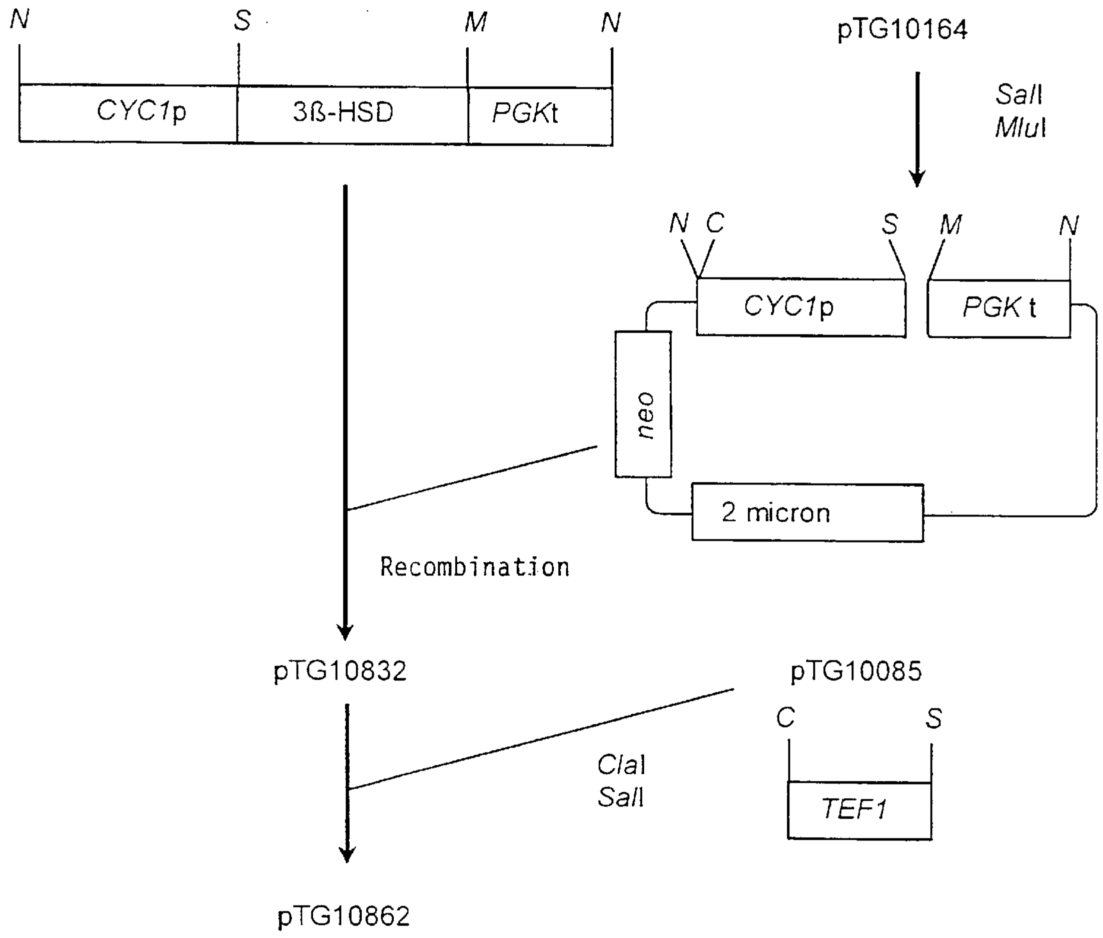

FIGS. 7A, 7B and 7C show the scheme of construction of the expression plasmids of human 3β-HSD in yeast, pTG10832 and pTG10862. FIG. 7A describes production of the MscI-MluI fragment containing the sequence coding for human 3β-HSD. The oligonucleotide sequence disclosed in FIG. 7A is that of OTG4461 (SEQ ID NO:7). FIG. 7B describes production of the NotI fragment containing the $CYC1_p$/3β-HSD/$PGK_t$ expression block. FIG. 7C describes production of the pTG10832 plasmid and of the pTG10862 plasmid.

Figure 8:
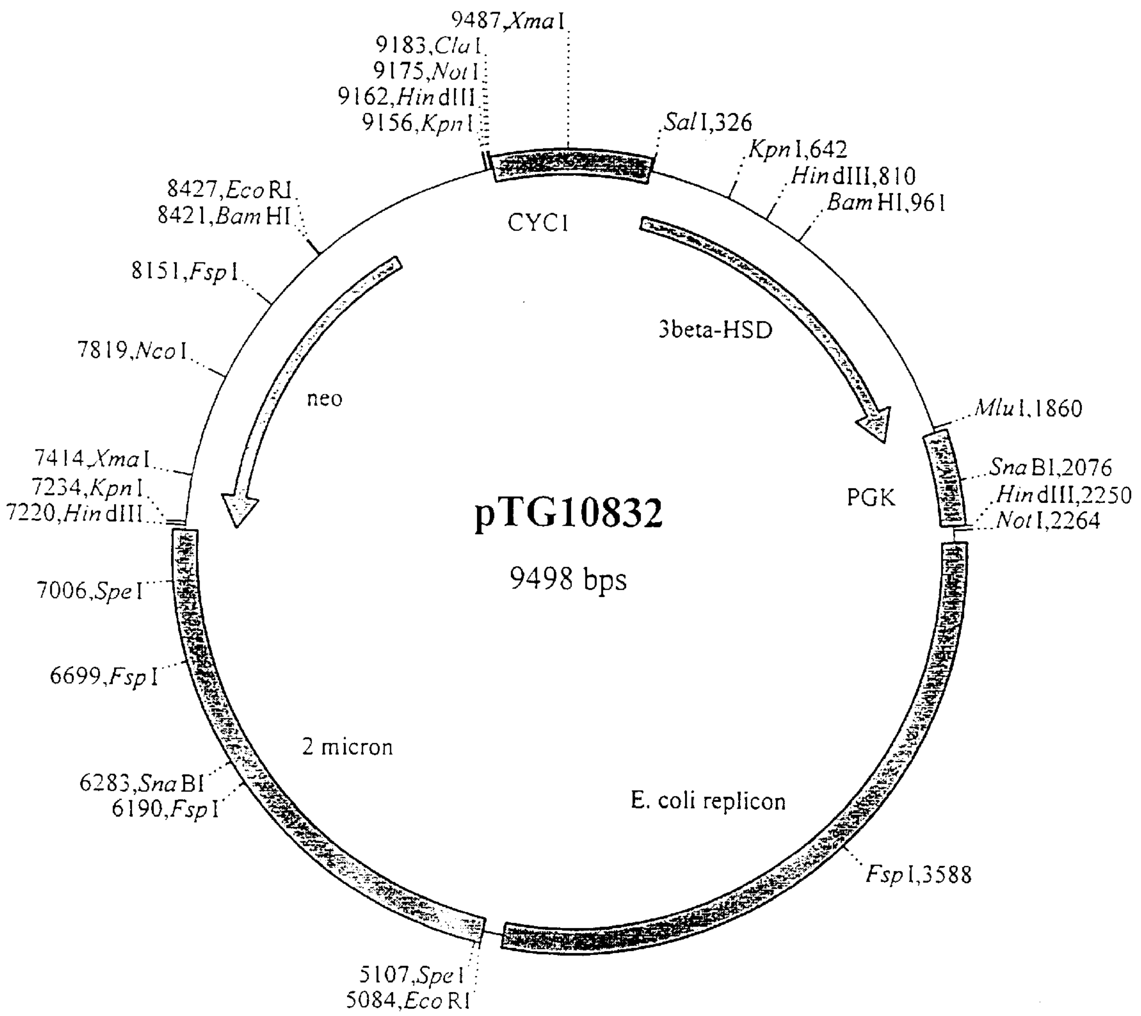

FIG. 8 shows a restriction map of plasmid pTG10832.

Figure 9:
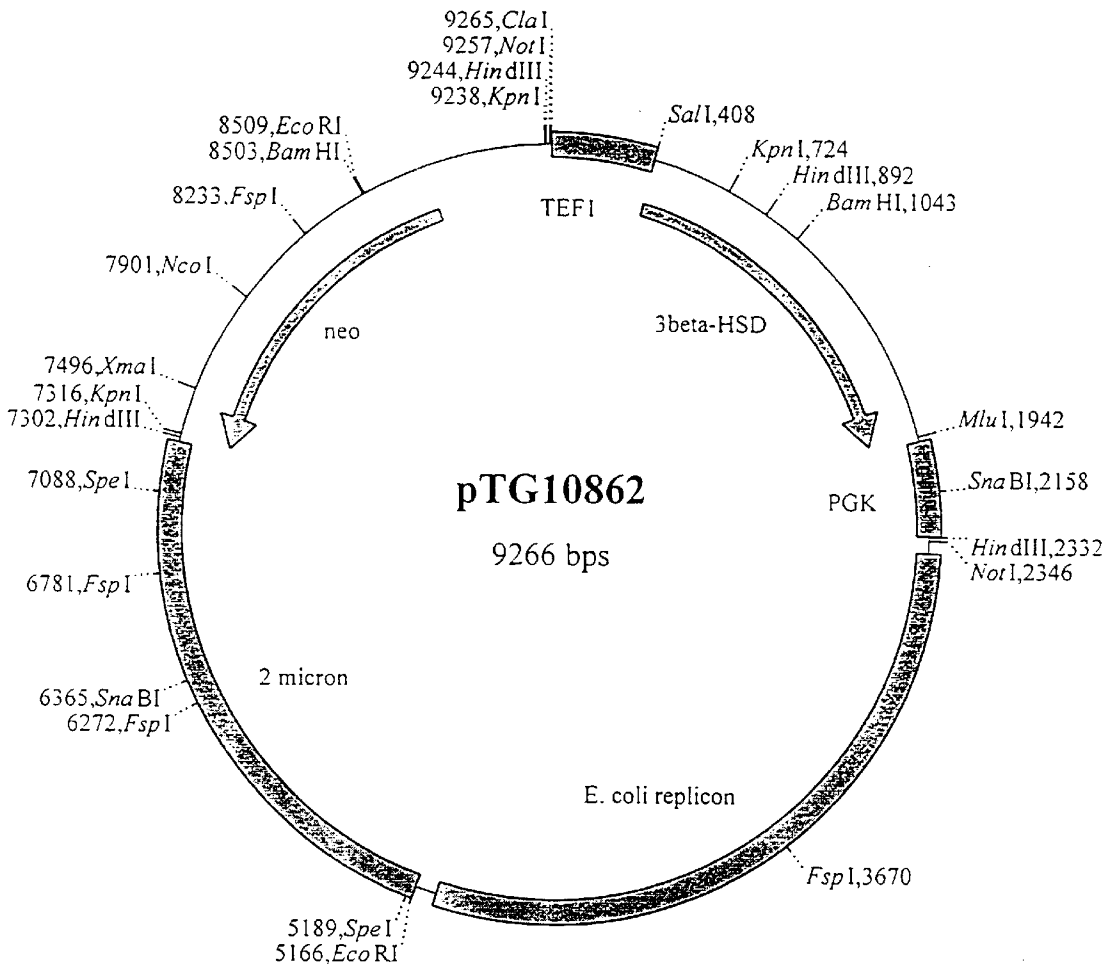

FIG. 9 shows a restriction map of plasmid pTG10862.

Figure 10:
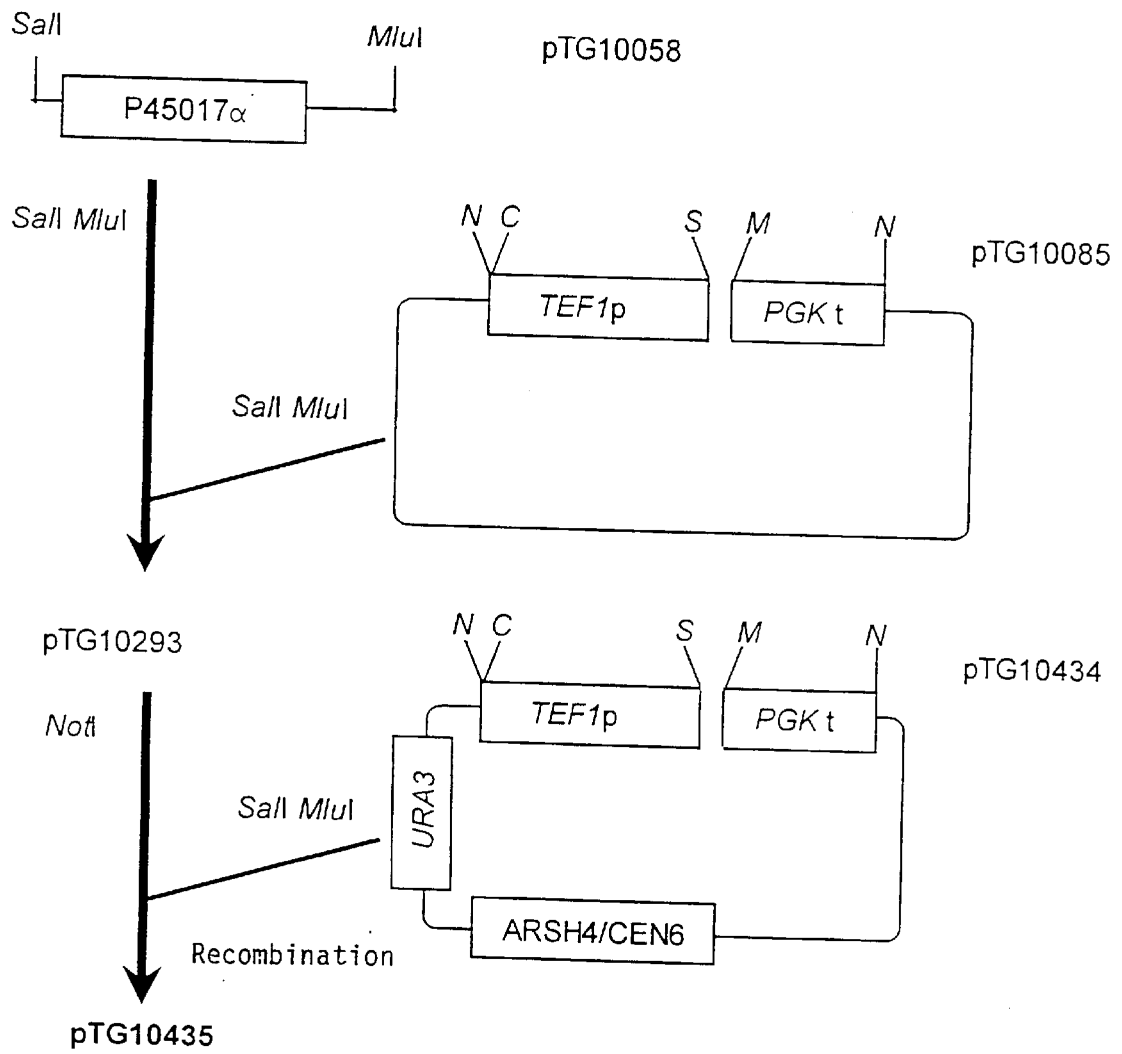

FIG. 10 shows the scheme for construction of the expression plasmid pTG10435.

Figure 11:
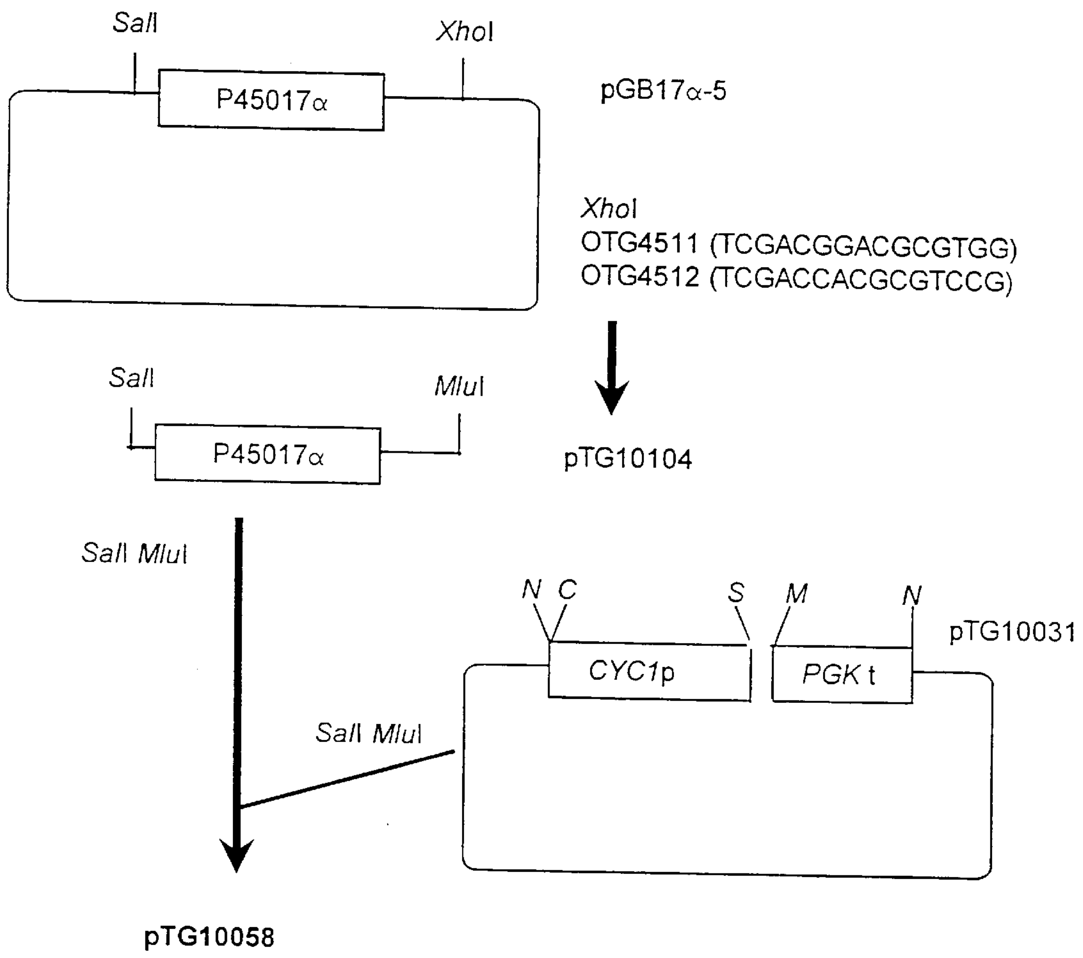

FIG. 11 shows the scheme for construction of the plasmid pTG10058.

Figure 12:
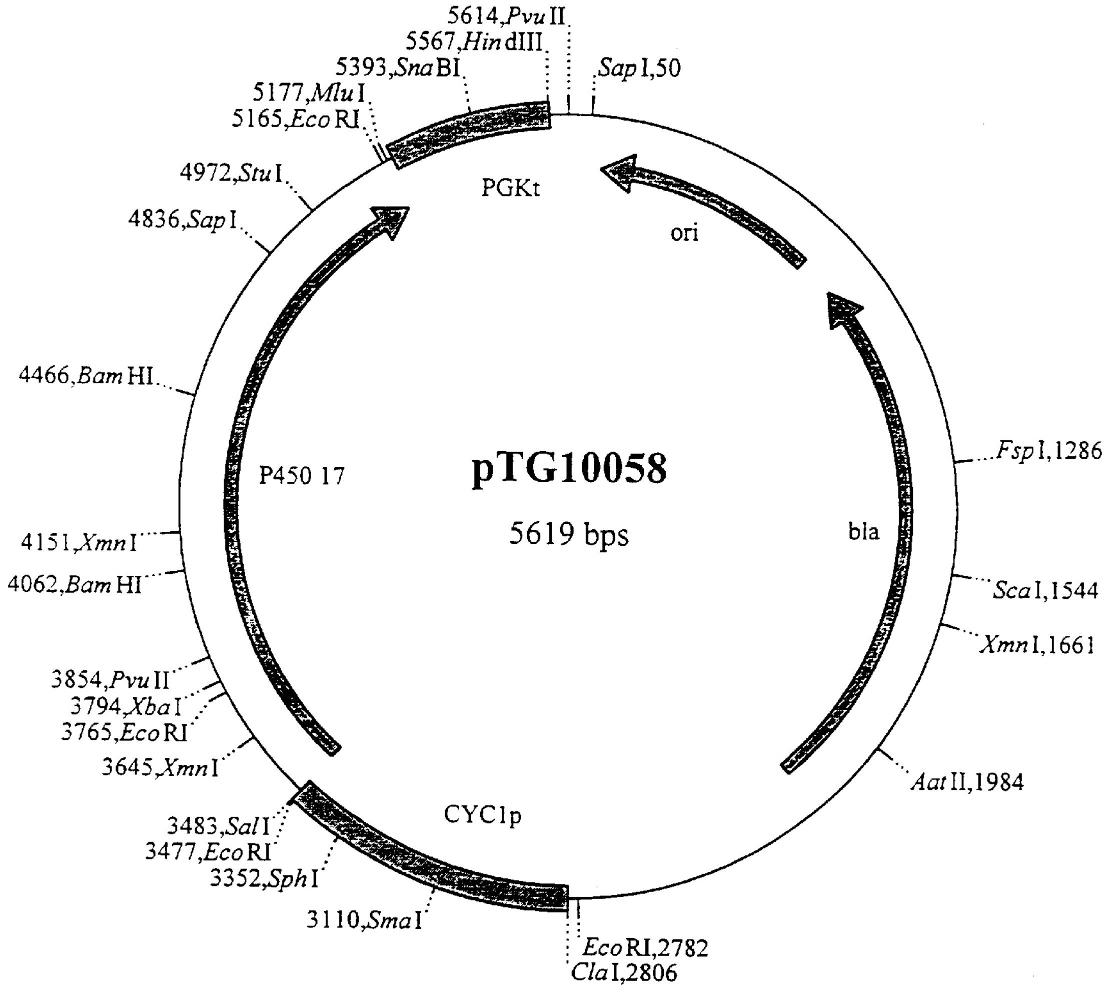

FIG. 12 shows a restriction map of plasmid pTG10058.

Figure 13:
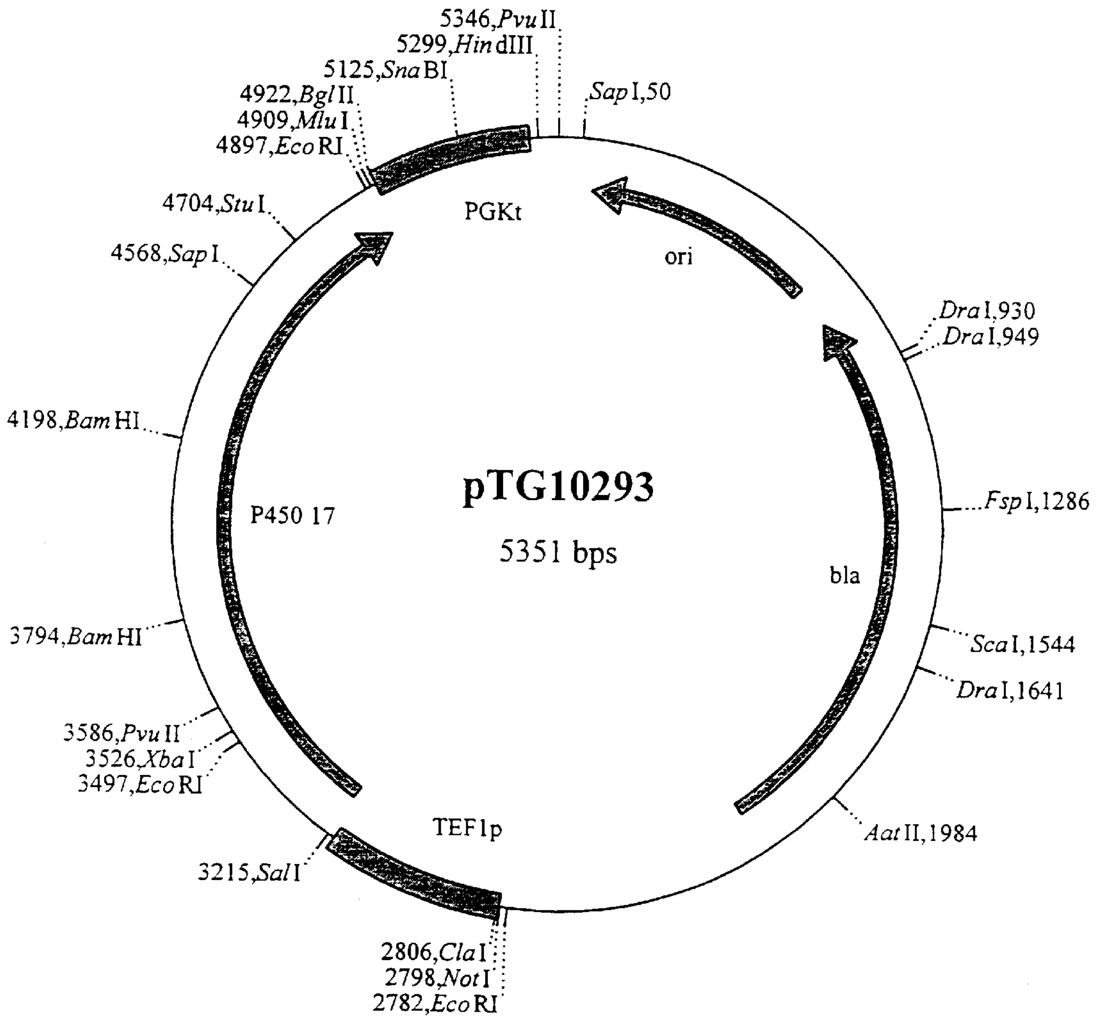

FIG. 13 shows a restriction map of plasmid pTG10293.

Figure 14:
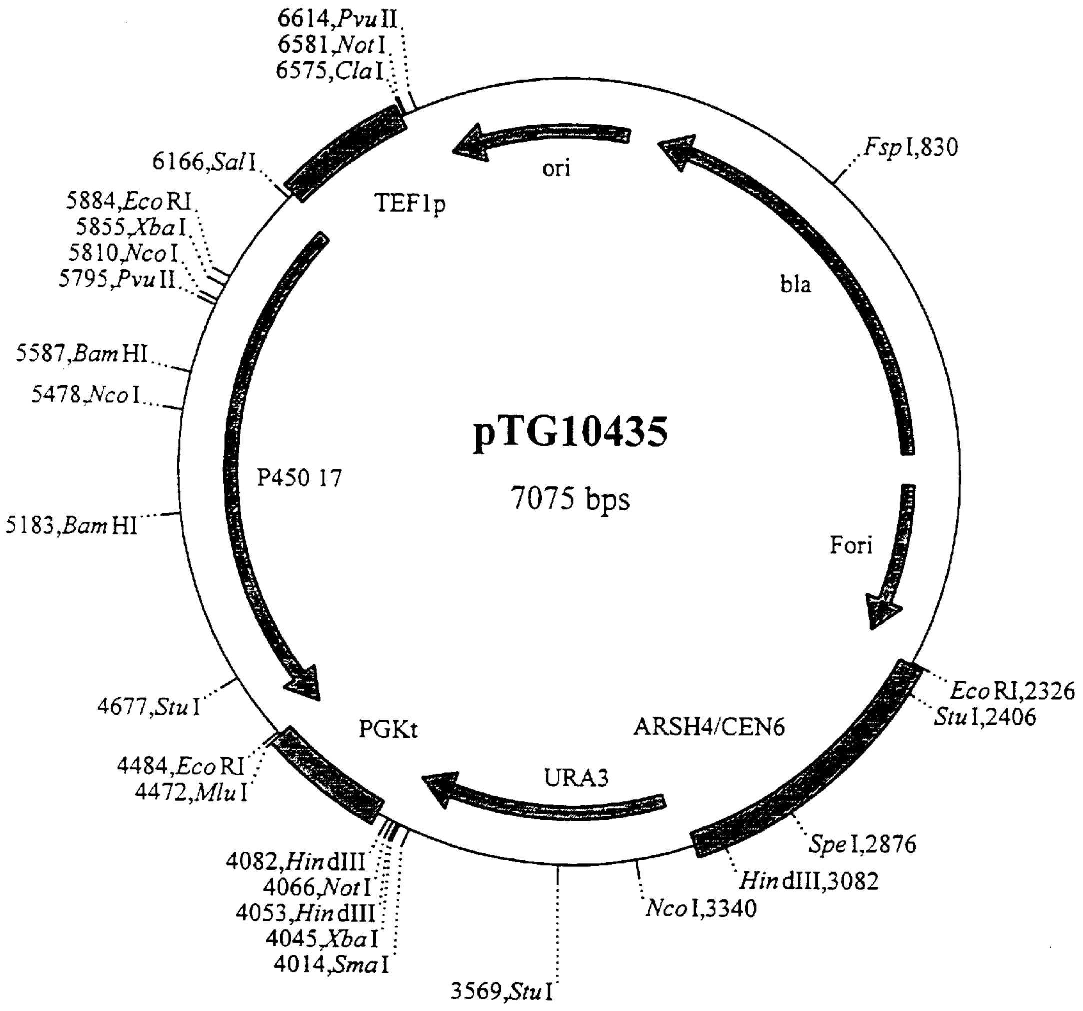

FIG. 14 shows a restriction map of plasmid pTG10435.

Figure 15A:
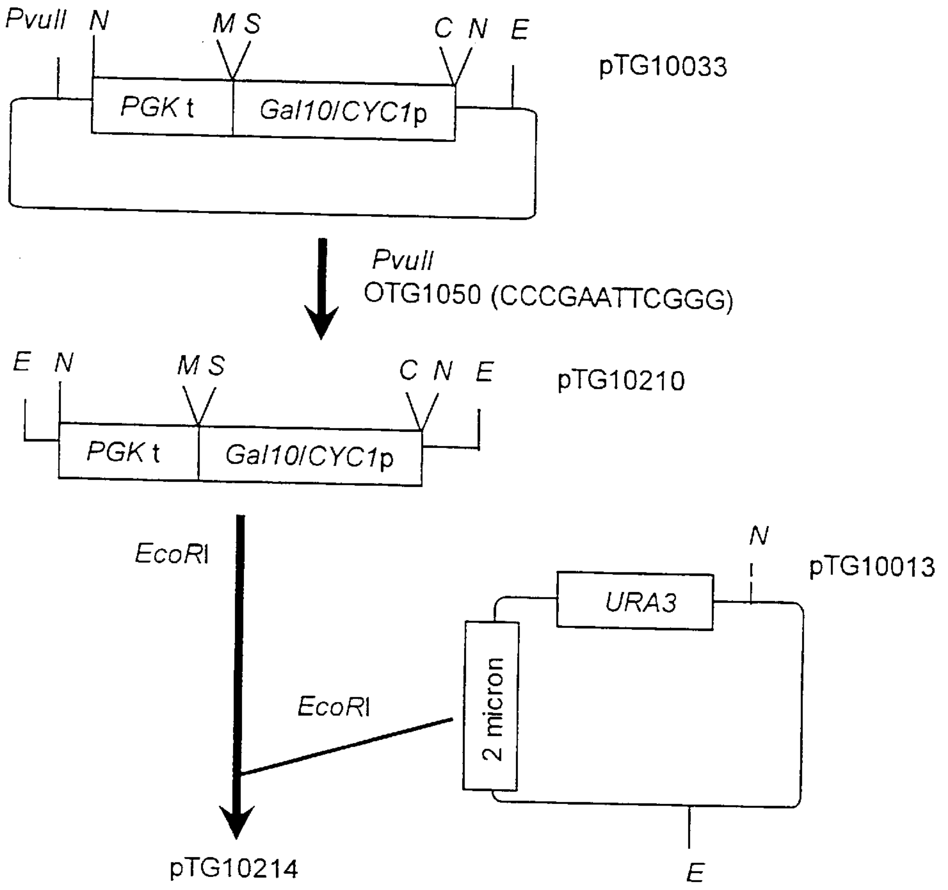
Figure 15B:
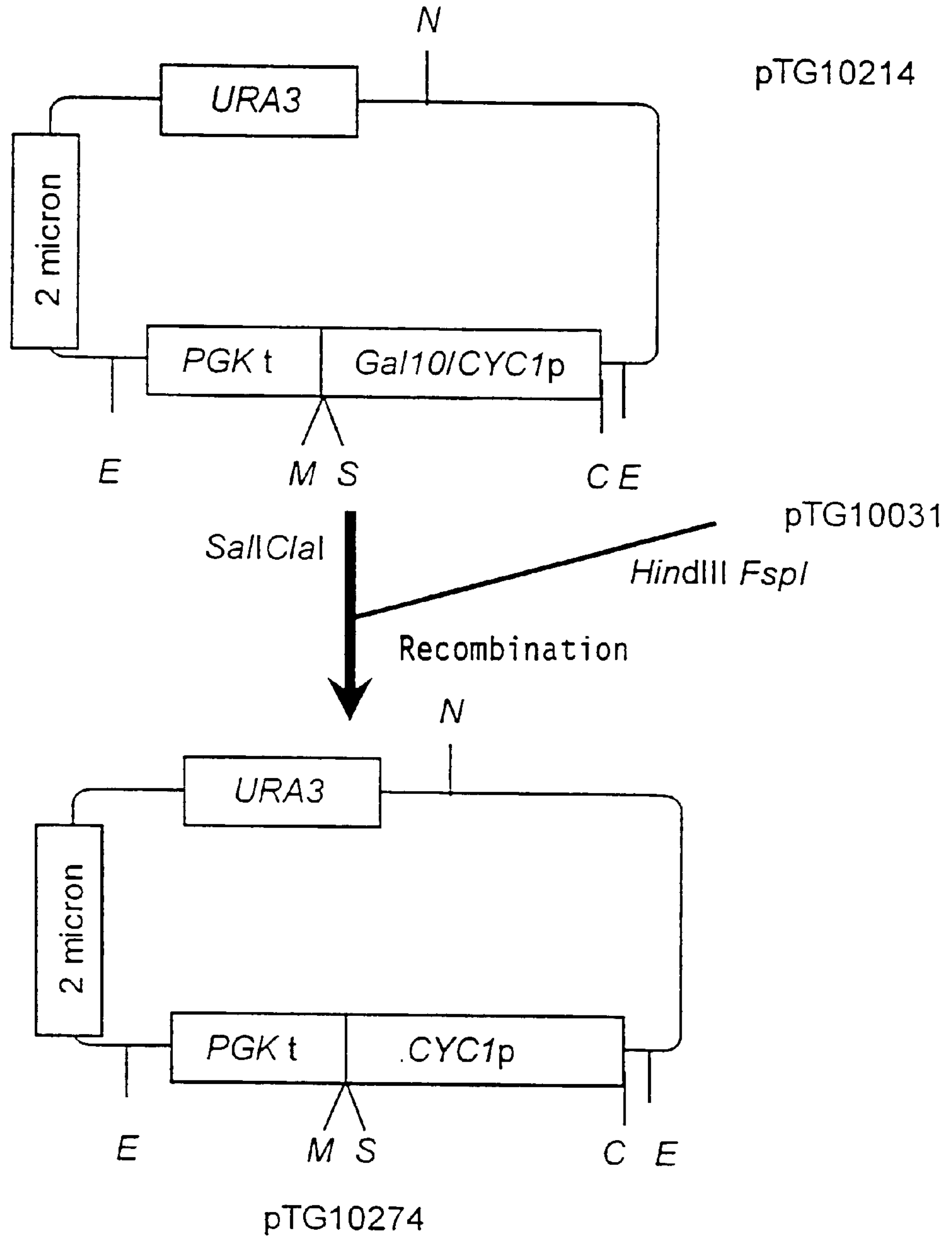

FIGS. 15A and 15B show the scheme of construction of plasmid pTG10274.

FIG. 15A describes the production of plasmid pTG10214.

FIG. 15B describes the production of plasmid pTG10274.

Figure 16:
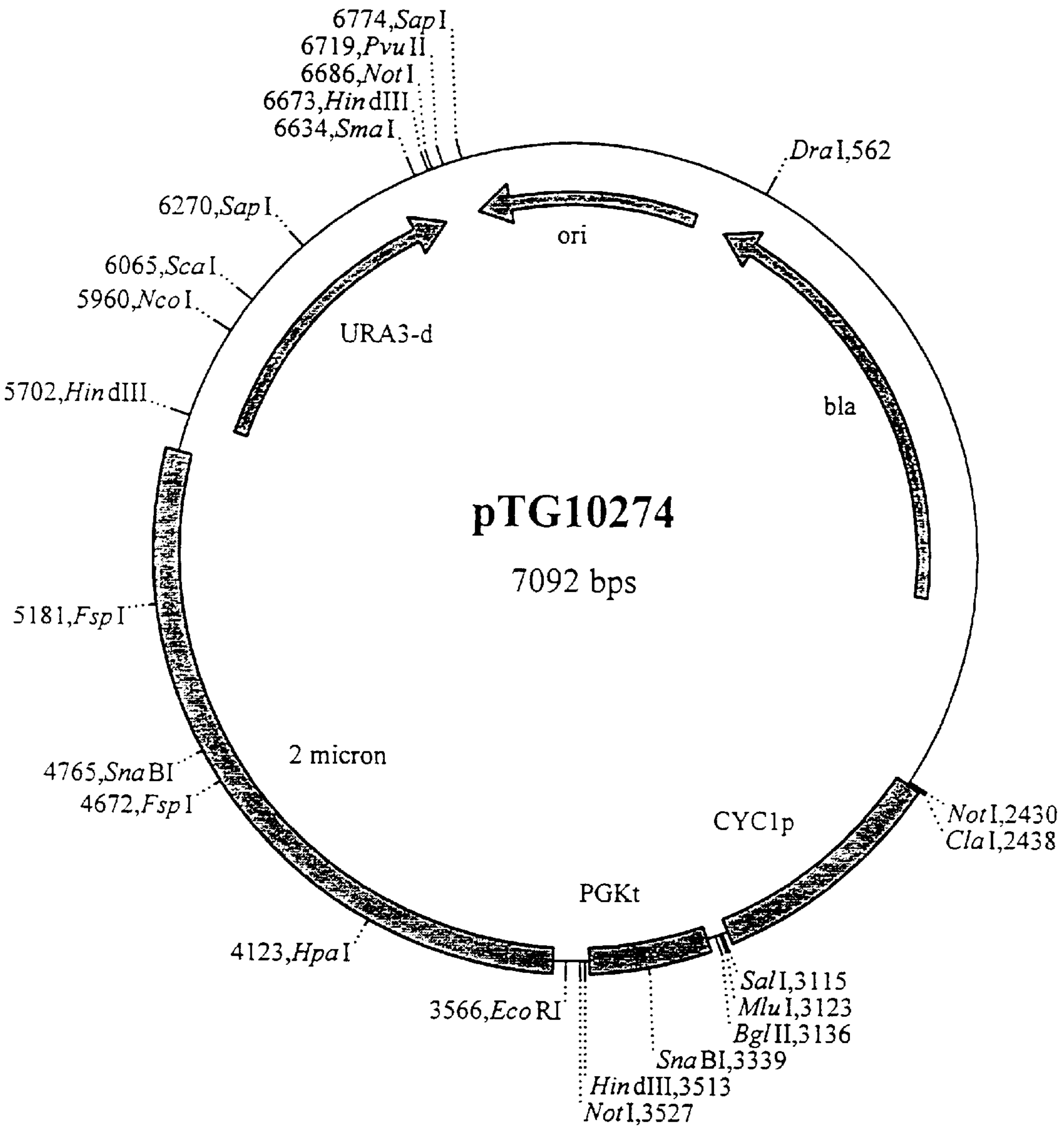

FIG. 16 shows a restriction map of plasmid pTG10274.

Figure 17:
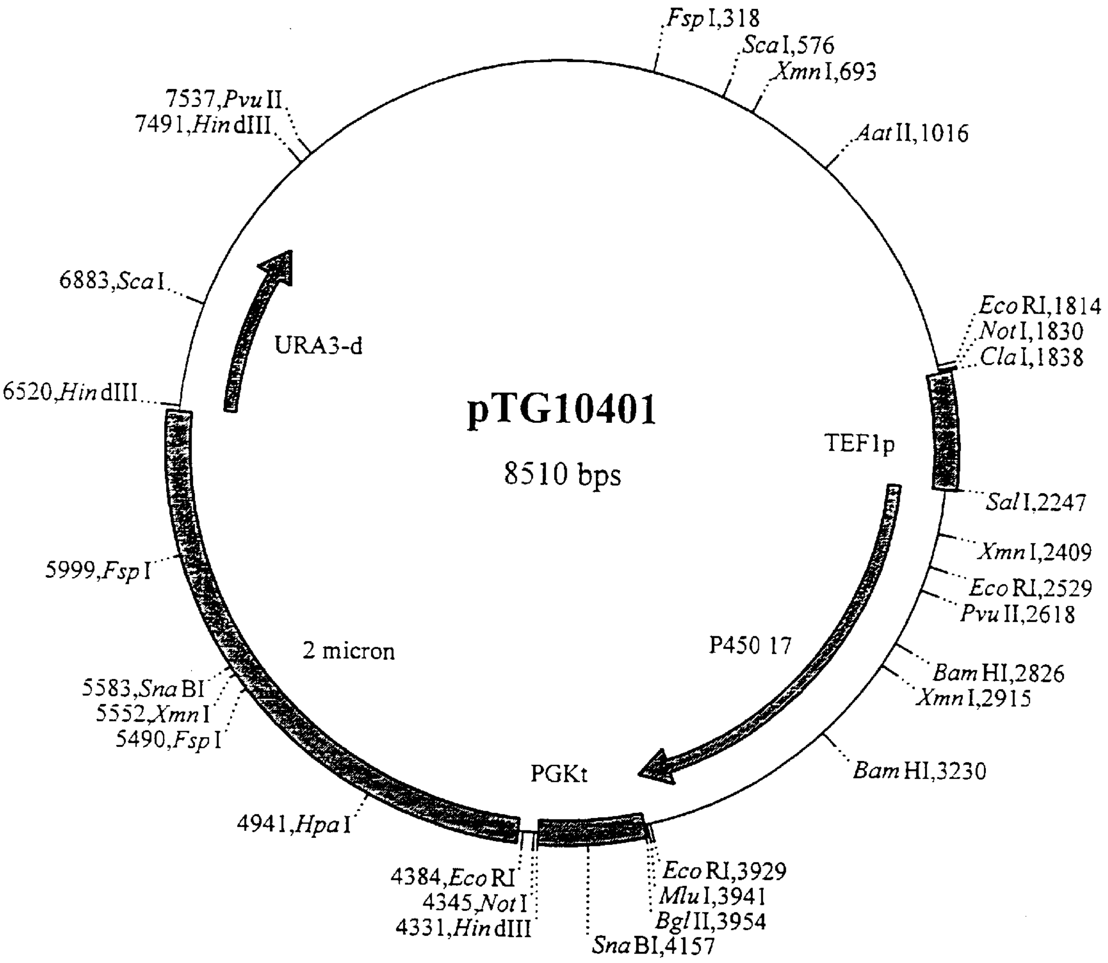

FIG. 17 shows a restriction map of plasmid pTG10401.

Figure 18:
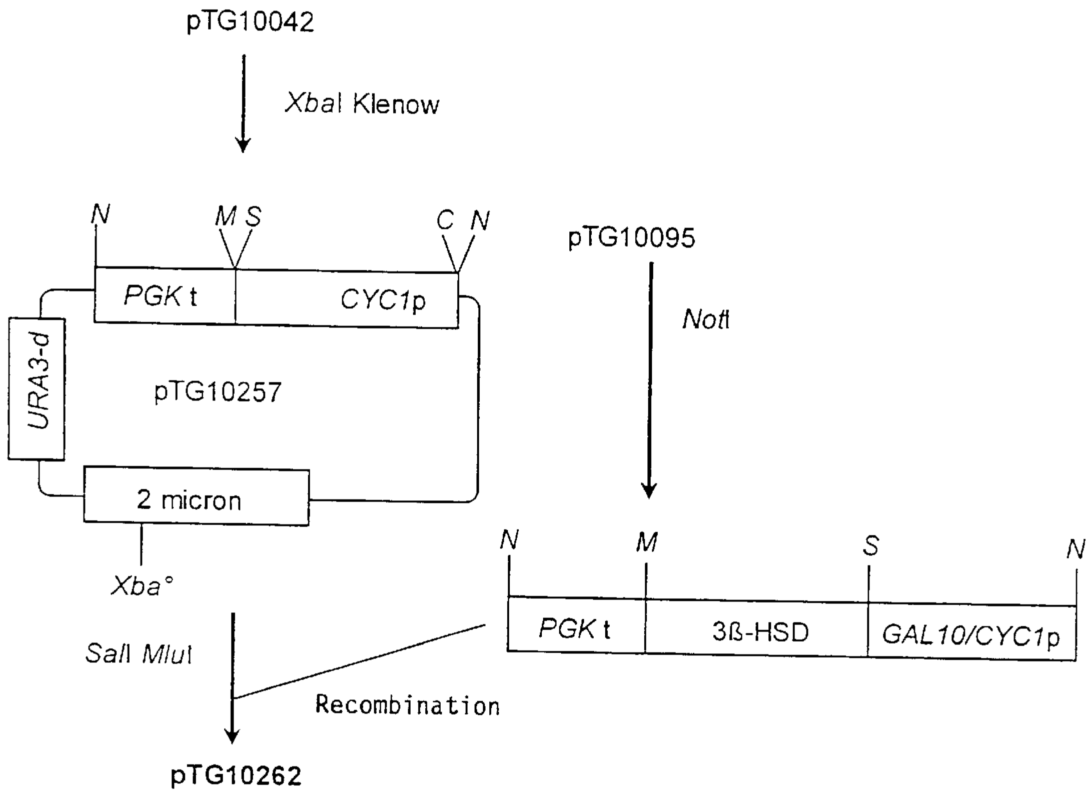

FIG. 18 shows the scheme for construction of the expression vector pTG10262.

Figure 19:
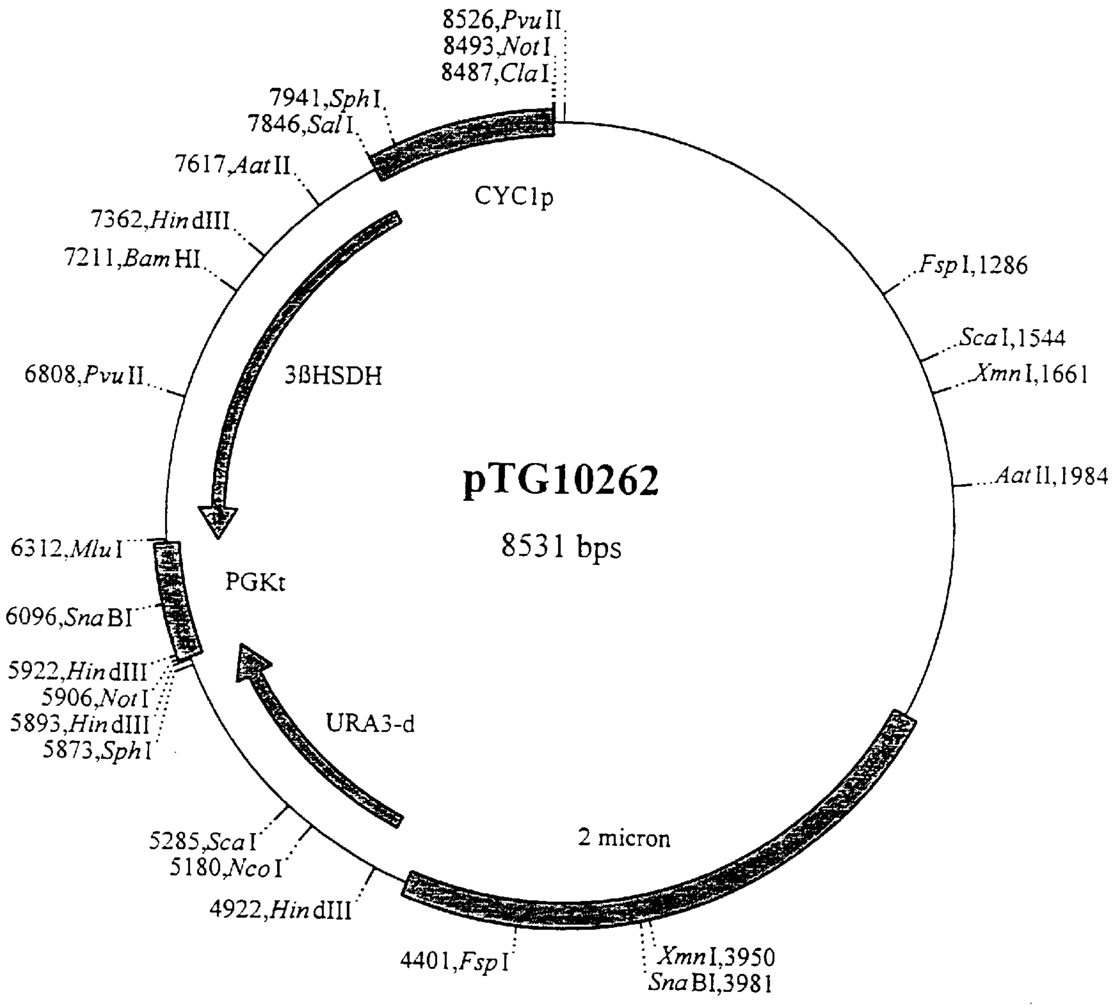

FIG. 19 shows a restriction map of plasmid pTG10262.

Figure 20:
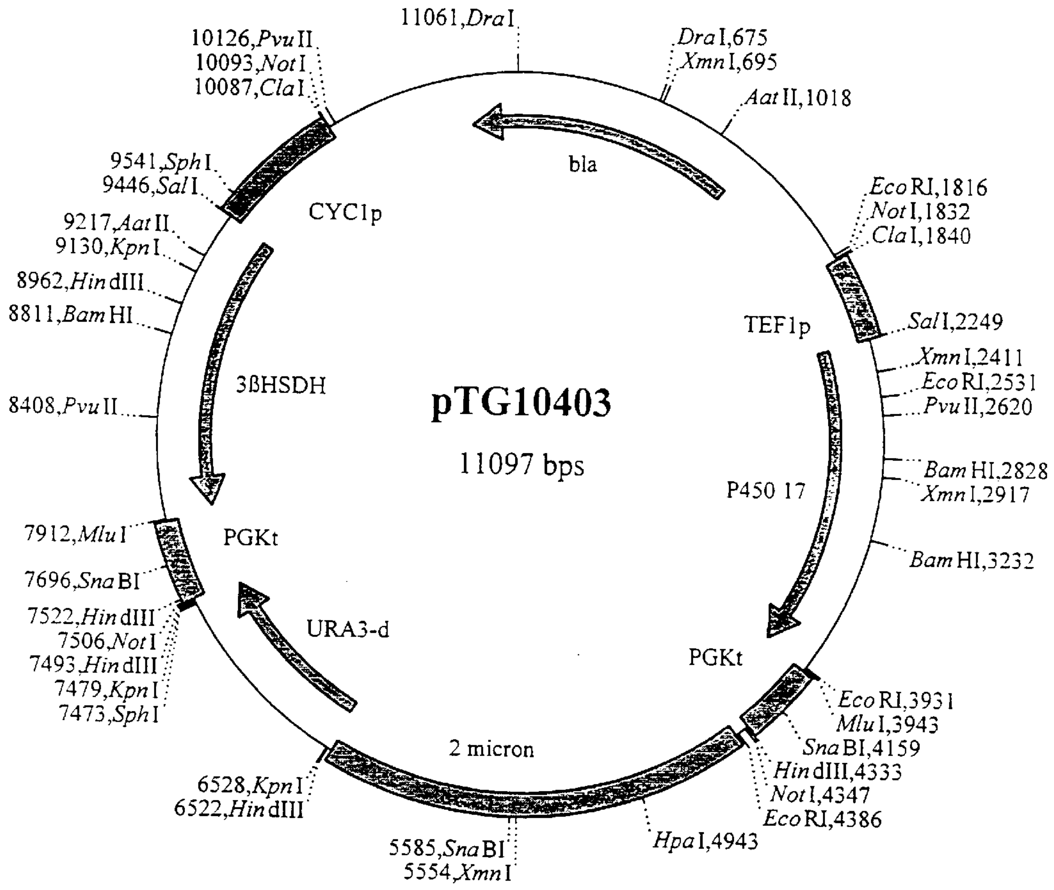

FIG. 20 shows a restriction map of plasmid pTG10403.

Figure 21:
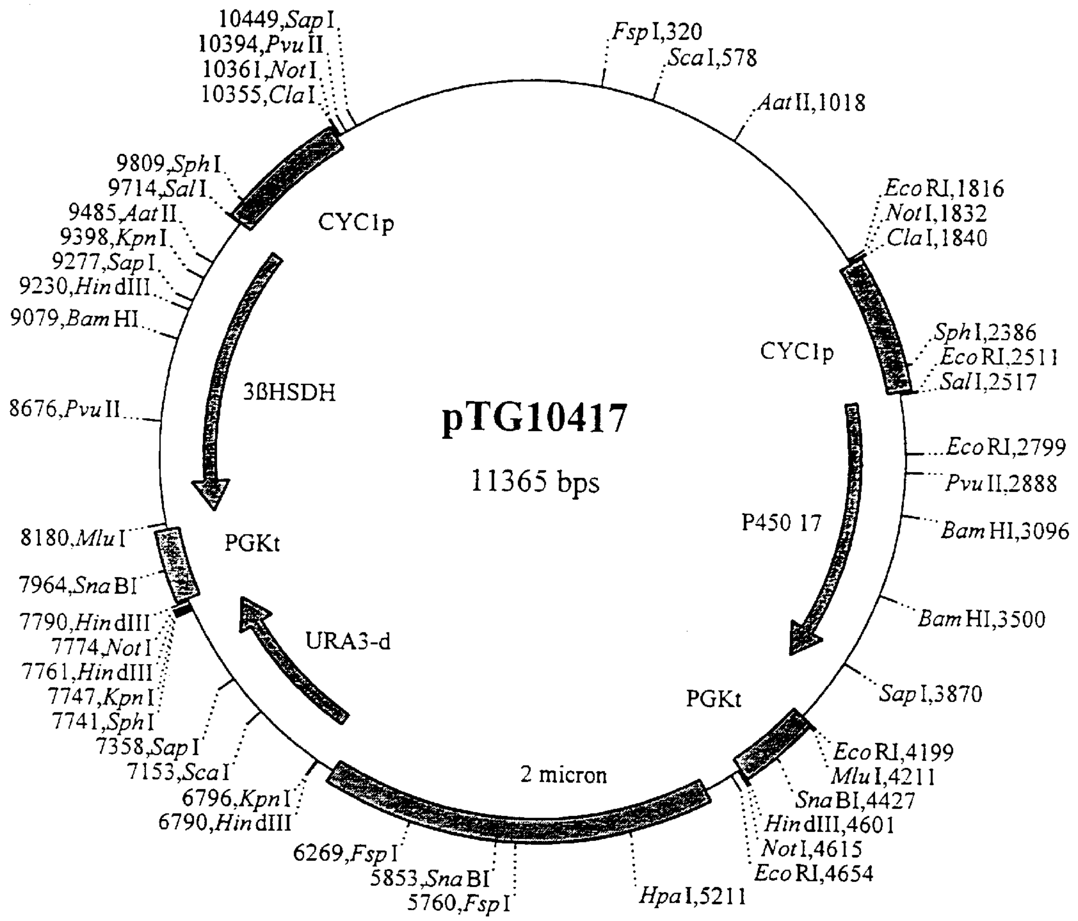

FIG. 21 shows a restriction map of plasmid pTG10417.

(Abbreviations of the restriction enzymes: S, SalI; N, NotI; BII, BglII; M, MluI, C, ClaI; N°, lost NcoI site; XbaI°, lost XbaI site; E, EcoRI).

EXAMPLE 1

Identification of the APAT Activity of the Yeast.

A—In-vivo Acetylation of Pregnenolone by Yeast.

The TGY73.4 strain was cultivated at 28° C. in 10 ml of YPD medium (Difco) inoculated at A600=0.1 from a 24 h preculture to which was added 100 μl of a solution of pregnenolone at 10 mg/ml in a tergitol (Sigma)/ethanol mixture (1:1). The steroids formed were identified on 250 μl aliquots of broth taken at intervals of time for 10 h. After extraction with 2 ml of dichloromethane, the organic phases were evaporated under nitrogen, then the residues obtained were redissolved in acetonitrile. The steroids were analysed by RP-HPLC on an Ultrasphere ODS column (Beckman) with the following successively as eluent: acetonitrile at 60% in water for 10 min, then acetonitrile varying from 60 to 80% in water for 5 min, then acetonitrile at 80% for 5 min at a flow rate of 1 ml/min, at 45° C. and with detection at 205 nm.

Figure 1:
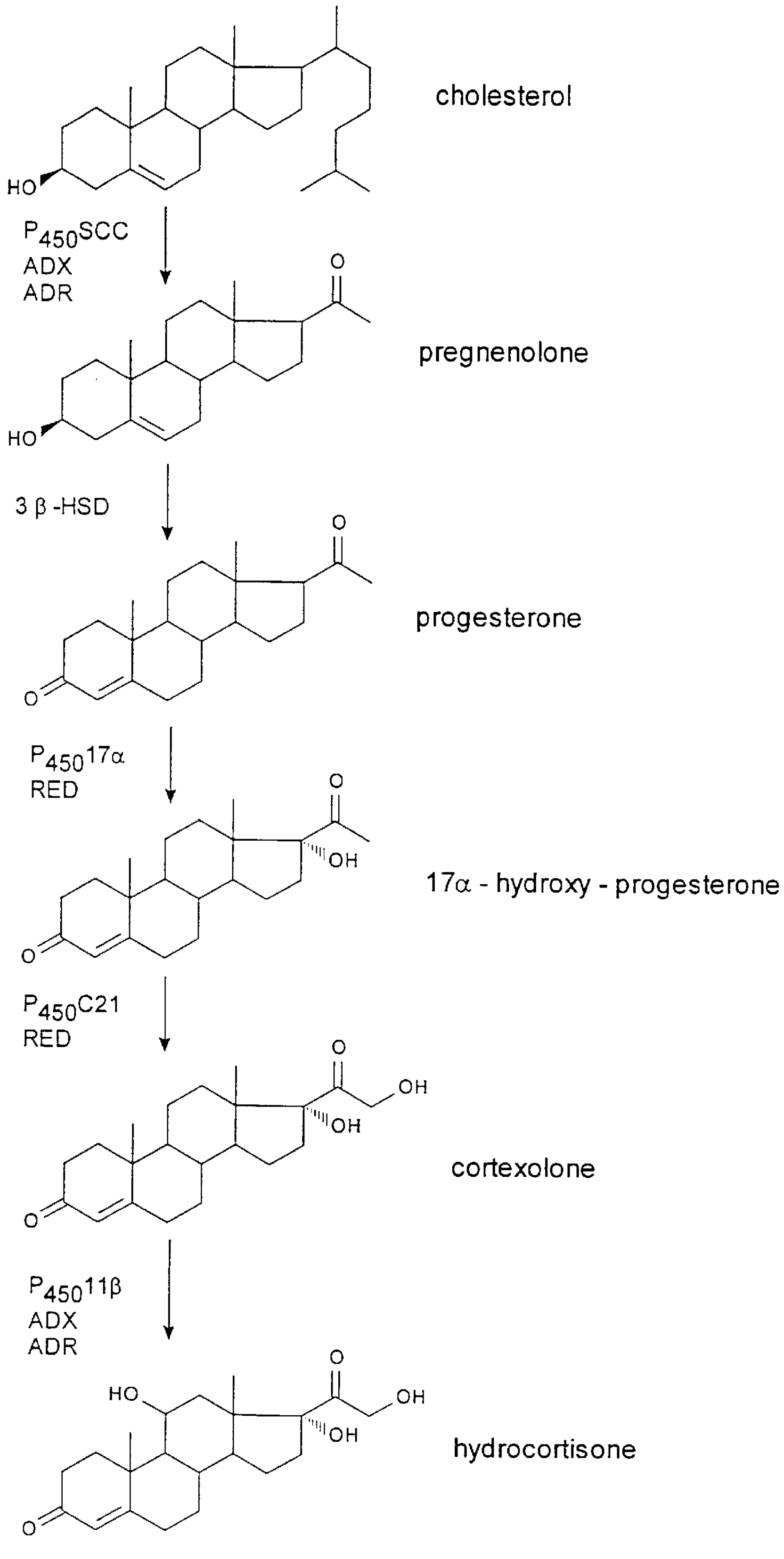
Figure 2A:
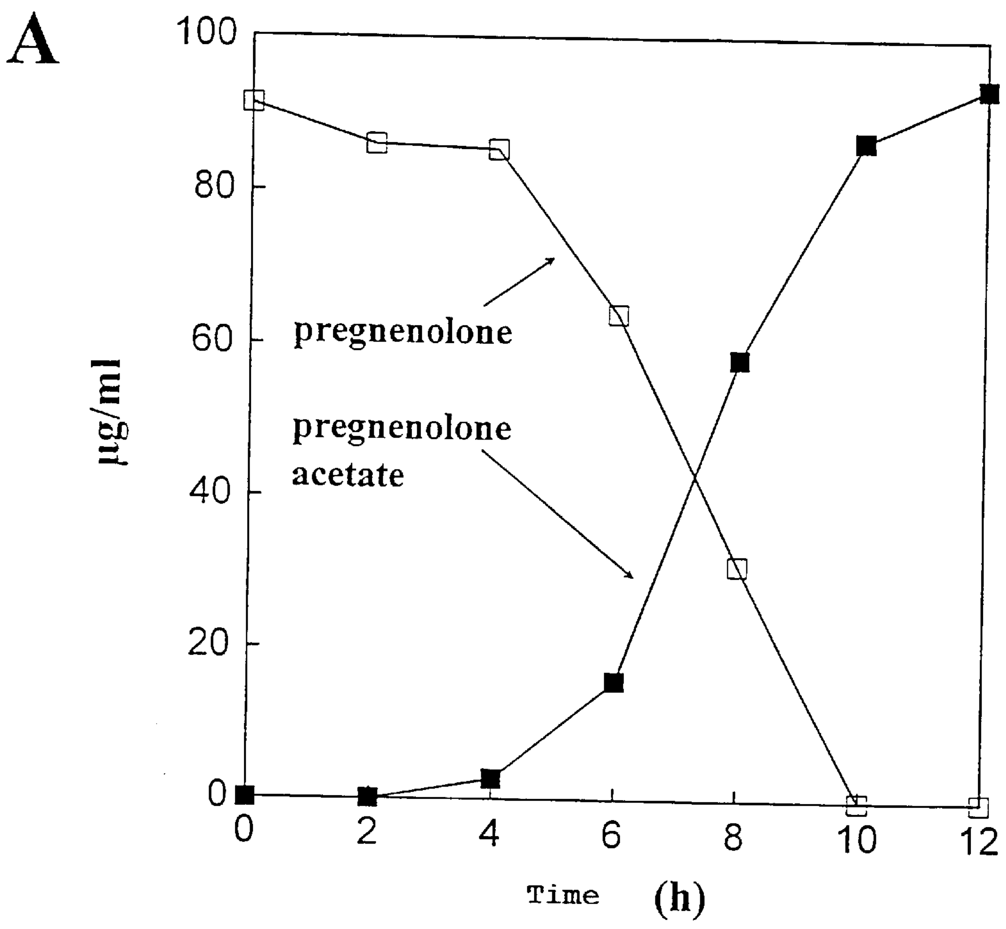
Figure 2B:
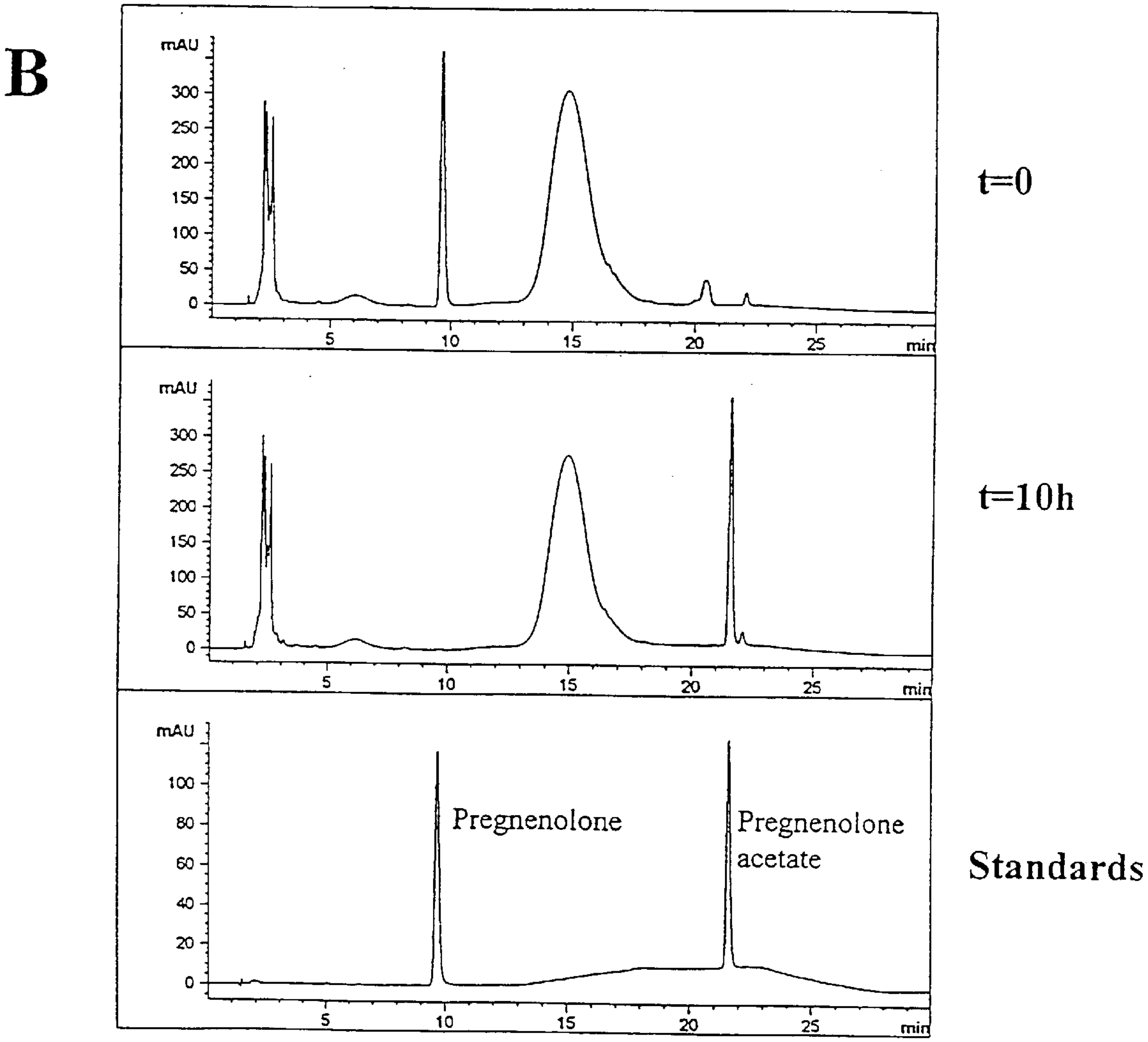

The chromatograms obtained (FIG. 2B) show that pregnenolone is metabolized to a more apolar product that possesses a TR identical to that of the pregnenolone acetate standard. FIG. 2A shows that the pregnenolone is rapidly converted by the yeast to its metabolite.

After alkaline treatment (KOH at 6% in methanol), the metabolite observed releases a product that has a TR identical to that of pregnenolone. Identification of the metabolite as pregnenolone acetate was then confirmed by mass spectrometry.

B—Purification of the Enzyme Possessing APAT Activity.

The TGY73.4 strain was cultivated in a 10-litre fermenter in Käppeli medium (Fiechter et al., 1981) enriched with glucose at 160 g/l at 30° C. up to A600=30. The cells were separated by centrifugation, washed with water then resuspended in 4 litres of Tris-HCl buffer 20 mM, pH 8.0 at 4° C. (buffer A) containing 1 mM of PMSF. The cells were disrupted in a Manton Gaulin homogenizer at a pressure of 1000 psi. The cell lysate obtained was centrifuged at 12,000×g for 15 min at 40° C., then zinc chloride was added to the supernatant to a final concentration of 40 mM. The pH was adjusted to 5.5 with 1N HCl and precipitation was effected for 30 min at 4° C. After centrifugation at 10,000×g for 10 min at 4° C., the precipitate was isolated and resuspended in 3 litres of buffer A containing 100 mM EDTA and 1 mM PSFM. After removing the EDTA by diafiltration on a Y10S10 cartridge (Amicon) against 30 litres of buffer A, the retentate was charged at a rate of 35 ml/min and at 4° C. in a column of 1.5 litres of DEAE-Sephacel (Pharmacia) previously equilibrated with buffer A. After washing the column with buffer A, then with buffer A containing 0.15 M NaCl, the APAT activity was eluted with buffer A containing 0.4 M NaCl. The fractions of DEAE-Sephacel containing the APAT activity, measured as indicated above in "General Materials and Methods", were combined, NaCl was added to a final concentration of 2 M, then they were charged at a rate of 15 ml/min and at 4° C. in a column of 500 ml of Phenyl-Sepharose (Pharmacia) previously equilibrated in buffer A containing 2 M NaCl. After washing the column with buffer A containing 0.5 M NaCl, the APAT activity is eluted with 1.5 litres of a linear gradient of sodium cholate varying from 0 to 1% in buffer A. The fractions containing the APAT activity were combined, then concentrated by ultrafiltration on a YM10 membrane (Amicon), then stored at −80° C. until use.

The whole process was repeated once so as to prepare the material in sufficient quantity to continue purification.

The material purified from the two aforementioned preparations was thawed, then charged at a rate of 4 ml/min and at 4° C. in a column of 100 ml of Q-Sepharose Fast Flow (Pharmacia) previously equilibrated in buffer A. After washing the column with the same buffer, the APAT activity was eluted with 500 ml of a linear gradient of NaCl varying from 0 to 1 M in the same buffer. The fractions of Q-Sepharose containing the APAT activity were combined and then charged directly at a rate of 2.5 ml/min and at 4° C. in a column of 7 ml of sodium cholate immobilized on Sepharose beads (Pharmacia) previously equilibrated with buffer A containing 0.5 M NaCl. After washing the column with the same buffer, the APAT activity was eluted with 100 ml of a linear gradient of sodium cholate varying from 0 to 1% in the same buffer. The fractions containing the APAT activity were combined, concentrated by ultrafiltration on a YM10 membrane (Amicon) to a protein concentration of 1.8 mg/ml, then stored at −80° C.

The APAT activity was thus purified about 500 times on the basis of the specific activity and with a yield of about 16% as shown in Table 1 below:

TABLE 1

| Stage | APAT activity (units) | Protein (mg) | Specific activity (units/mg) | Purification | Yield |
|---|---|---|---|---|---|
| Supernatant 12,000 g | 8.057 | 42.242 | 0.19 | 1 | 100 |
| Precipitation with zinc | 10.453 | 28.040 | 0.37 | 1.9 | 129 |
| DEAE-Sephacel | 6.399 | 5.009 | 1.28 | 6.7 | 79 |
| Phenyl-Sepharose | 3.316 | 489 | 6.78 | 35.7 | 41 |
| Q-Sepharose | 1.712 | 39 | 43.9 | 231 | 21 |
| Cholate-Sepharose | 1.300 | 13 | 100 | 526 | 16 |

Figure 3:
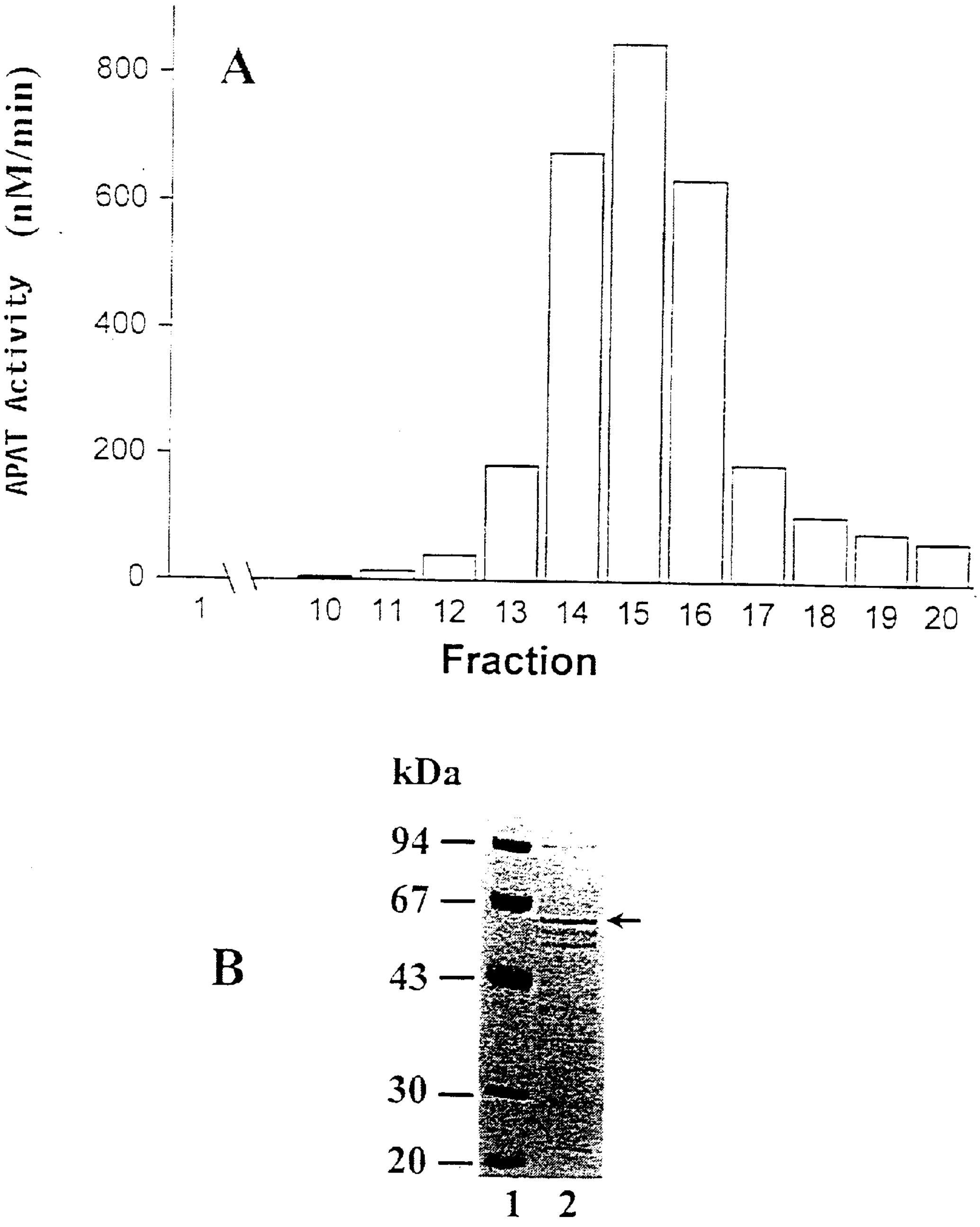

Half of the semi-purified material obtained above (about 6 mg of protein) was then thawed and PEG 4000 (Prolabo)

was added to a final concentration of 20% (w/v) to eliminate the cholate and the NaCl. After stirring for 30 min at 4° C., the precipitate was collected by centrifugation at 12,000×g for 30 min at 4° C., then redissolved in 4 ml of buffer A. The solution thus obtained was then charged at a rate of 1 ml/min in a column of MonoP HR5/20 (Pharmacia) previously equilibrated with buffer bis-Tris 25 mM pH 6.3. The APAT activity was eluted with buffer Polybuffer 74 pH 4.0 (Pharmacia). 1 ml fractions were collected, each in the presence of 50 $\mu$l of buffer Tris-HCl 2 M, pH 8.0 so as to limit the inactivation of the enzyme at acid pH. Fractions 14, 15 and 16 (FIG. 3(A)) containing the highest APAT activity, measured as indicated above, were combined, concentrated by ultrafiltration on YM10 membrane, then stored at −80° C. before use. The active fraction thus obtained was submitted to SDS-PAGE on gel with 10% polyacrylamide. Several bands were revealed by staining with Coomassie blue with a majority band with an apparent MW of 62 kDa (FIG. 3(B)), identical to the MW determined by filtration on gel of Superose 6 (Pharmacia) and corresponding to the APAT activity.

C—Properties of APAT.

a) Substrate Specificity

According to the method stated above for acetyl-CoA and pregnenolone, using different acyl donors or different steroid substrates, the semi-purified APAT transfers the acetate on 3β-ol, delta$^4$ or delta$^5$-steroids with comparable efficiency whereas transfer is slight on oestrogens and not detectable on sterols and with a marked preference for acetyl-CoA as acyl donor.

Table 2 below, in which for a) the tests are effected with 30 $\mu$M of each steroid tested and 100 $\mu$M of [$^3$H]acetyl-CoA and for b) the tests are effected with 100 $\mu$M of each acyl donor and 30 $\mu$M of [$^3$H]pregnenolone, shows the results obtained:

TABLE 2

| Substrate a) | Relative activity (%) | Substrate b) | Relative activity (%) |
|---|---|---|---|
| Pregnenolone | 100 | acetyl-CoA | 100 |
| 17α-OH pregnenolone | 89 | propionyl-CoA | 33 |
| DHEA | 104 | butyryl-CoA | 16 |
| 4-pregnen-3βol-20-one | 70 | hexanoyl-CoA | 18 |
| 5β-pregnan-3βol-20-one | 1.8 | oleoyl-CoA | not detected |
| 17β-oestradiol | 5 | | |
| oestrone | 2.5 | | |
| cholesterol | 0.6 | | |
| ergosterol | 0.4 | | |

b) Inhibition

The APAT activity is strongly inhibited by reagents of sulfhydryl groups such as NEM and DTNB. Inhibition is complete in the presence of zinc chloride (1 mM).

D—Partial Amino Acid Sequence.

The partial amino acid sequence was determined after digestion with trypsin on gel sections according to the method described by Rosenfeld et al. (1992).

Starting from two thirds of the concentrate obtained above then separated by SDS-PAGE, the 62 kDa band was cut out then incubated with trypsin (Promega). The peptides generated were then separated by RP-HPLC on a Vydac 218TP column (1.5×125 mm) at a rate of 100 $\mu$l/min, using a linear gradient of acetonitrile varying from 0 to 60% in 80 min, then from 60 to 100% in 20 min in a 0.1% TFA solution in water and were then submitted to amino acid sequencing.

The N-terminal sequence was determined on a Model 477A protein sequencer connected to an HPLC analyser of PTH-amino acids (Applied Biosystems).

Among the samples sequenced, two peaks x and y give an unambiguous sequence made up respectively of the following 10 and 16 amino acids:

for peak x: ISEQFKKDDF (SEQ ID NO:18)

for peak y: LIELISPVIIPLGNPK (SEQ ID NO:19)

The two peptide sequences thus obtained were used for is screening the database of the genome of *S. cerevisiae*. A protein of 62 kDa whose sequence contains exactly the sequences of the above two peptides was identified (Mips, accession S64491, Hebling et al., May 1996). This protein whose sequence is shown in FIG. 4 and whose function has not been described would be coded by a gene at locus YGR177c. On the basis of identity of about 37% of the amino acid sequence between the protein of the invention possessing acyltransferase activity and the product of the ATF1 gene in *S. cerevisiae* described by Fujii et al. (1994) and to which an alcohol acetyltransferase has been attributed, we shall use the designation ATF2 for the gene coding for the protein responsible for APAT activity in *S. cerevisiae.*

EXAMPLE 2

Construction of Yeast Strains Possessing the ATF2 Gene Disrupted by the URA3 Gene and Which Have Lost APAT Activity (atf2-Δ::URA3).

A) Targeting of the ATF2 Gene.

The URA3 gene of *S. cerevisiae* was introduced by substitution of a selected part of the ATF2 gene of *S. cerevisiae* permitting subsequent selection of mutant strains by prototrophy with uracil.

Figure 5:
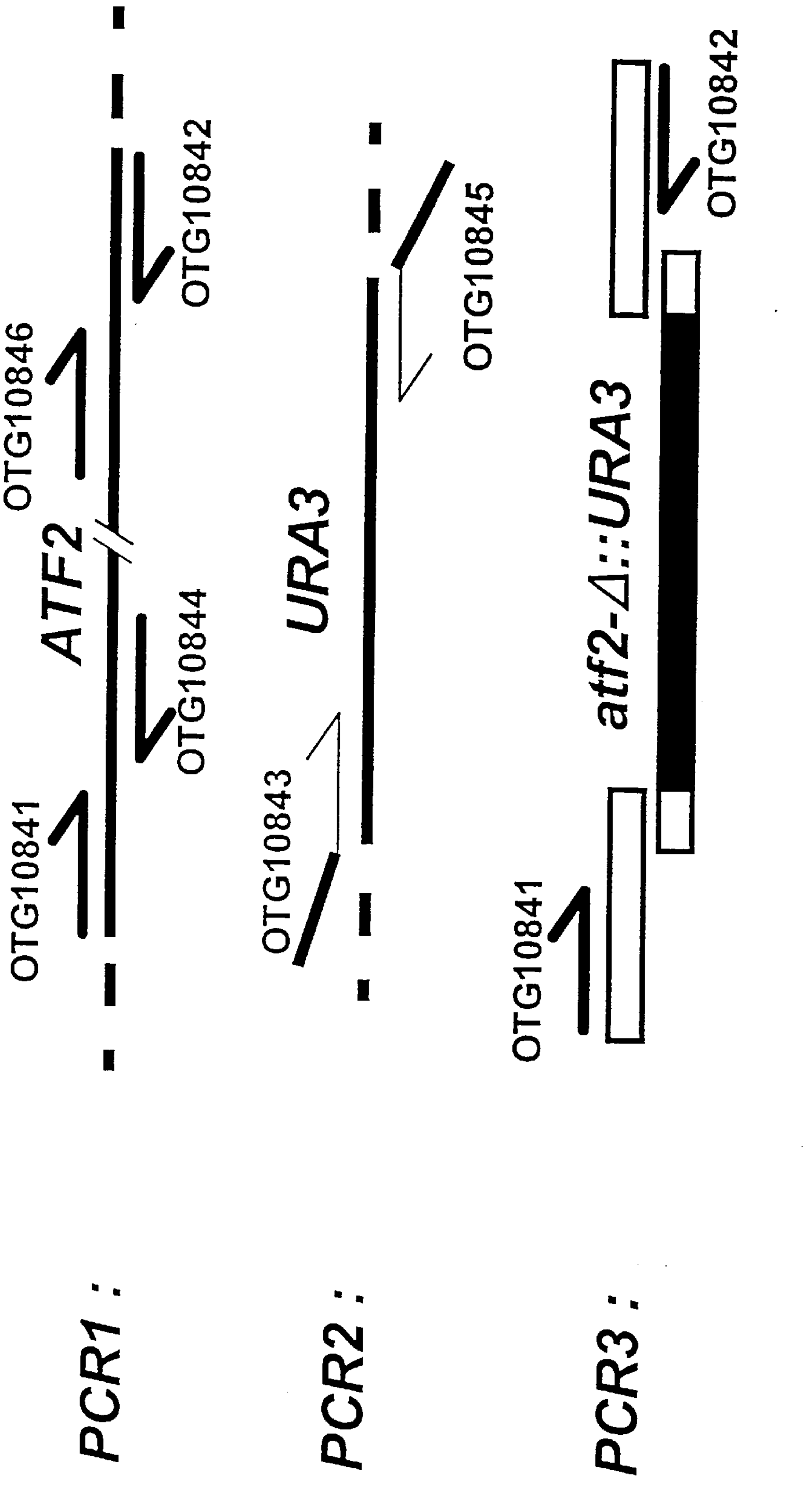
FIG. 5 shows the strategy of disruption of the ATF2 gene by combining with the URA3 gene by the double-fusion PCR technique. The empty bars and the filled bars represent the sequences of ATF2 and URA3 respectively.

The URA3 selection marker was combined with the ATF2 gene by double fusion PCR according to the method described by Amberg et al., 1995. The strategy followed, shown in FIG. 5, comprises a total of 4 PCR reactions. The first two reactions (designated PCR1) permit, respectively, amplification of the 5' and 3' regions flanking the insertion site of the URA3 marker in the ATF2 target gene that is disrupted, and the third reaction (designated PCR2) permits amplification of the URA3marker gene. Double fusion (designated PCR3) finally permits combining of the 5' and 3' regions of the ATF2 target gene with the URA3 marker gene (designated 5'ATF2-URA3-3'ATF2).

Firstly, a sample of intact cells of the Fyl679 strain used as source of DNA of the ATF2 target gene was amplified in the PCR buffer containing 2 mM DNTP (Pharmacia) in the following conditions: 25 cycles; 93° C., 30 s; 54° C., 2 min; 68° C., 3 min followed by an extension of 5 min at 72° C.; polymerase Ampli Taq (Perkin Elmer).

On the one hand, the 5' region of the ATF2 gene was amplified by PCR using, as direct and indirect primers, the oligonucleotides possessing the following sequences:

OTG10841: AAAAGTCGACAAAATGGAAGATATA-GAAGGATACGAA CCACATATCACTC (SEQ ID NO:1) and

OTG10844: ATCAATCTCCAATTAGGC CTCTTCG-GATTACCC (SEQ ID NO:2)

which contain a region homologous to the 5' region of the sequence of the ATF2 gene (SGD: YGR177c) and by adding a restriction site SalI for the OTG10841.

On the other hand, the 3' region of the ATF2 gene was amplified by PCR using, as direct and indirect primers, the oligonucleotides possessing the following sequences:

OTG10846: CATTCGACATTCCCGAAGGTGACAAT-GACAAG (SEQ ID NO:3) and

OTG10842: AAAAACGCGTAACTATTAAAGC-GACGCAAATTCGCCGATGGTTTGG (SEQ ID NO:4)

which contain regions homologous to the 3' region of the sequence of the ATF2 gene (SGD: YGR177c) and by adding a restriction site MluI for OTG10842.

Secondly, the URA3 gene of *S. cerevisiae* was amplified by PCR, using as direct primer the oligonucleotide possessing the sequence:

OTG10843:

GGGTAATCCGAAGAGGCCTAATTG-GAGATTGATAAGCTTTTCAA TTCAATTCAT-CATTTTTTTTTTATTCTTTTTTTTG (SEQ ID NO:5)

which contains a sequence homologous to the 5' region of the published sequence of the URA3 gene (Rose et al., 1984; GenBank: YSCODCD accession : K02207; SGD: YEL021w) combined with a sequence homologous to the 5' region of the ATF2 gene (complementary to OTG10844) and as indirect primer the oligonucleotide possessing the sequence:

OTG10845: CTTGTCATTGTCACCTTCGGGAAT-GTCGAATGGGGTAATAACTGATATAAT-TAAATTGAACTC (SEQ ID NO:6)

which contains a sequence homologous to the 3' region of the URA3 gene combined with a sequence homologous to the 3' region of the ATF2 gene (complementary to OTG10846). A 20 ng sample of DNA of the URA3 gene, isolated from the shuttle vector *E. coli*-yeast pTG10021 (Degryse et al., 1995) by digestion with the restriction enzyme HindIII was amplified in the conditions stated above.

The PCR products respectively obtained were purified using the "Geneclean kit" (Bio 101 Inc., La Jolla, USA), then submitted to the double fusion reaction, using as primers the aforementioned oligonucleotides OTG10841 and OTG10842 in the amplification conditions used for the previous PCR reactions with a programme of 20 cycles.

After purification of the final fusion product which contains the regions flanking the ATF2 gene fused to the functional URA3 gene, the presence of the URA3 gene was confirmed by digestion with the EcoRV restriction enzyme which shows the presence of this site in the amplified material.

B) Generation of Yeast Strains atf2-Δ::URA3.

The fusion product obtained above was transformed directly in the competent cells of strain Fyl679 or of strain TGY73.4 and the transformants were selected by growth on SD medium (F. Sherman, 1991) in the presence of the nutritional requirements of the strain and in the absence of uracil.

Starting from isolated clones, the new combination between the 5' region of the ATF2 gene and the URA3 gene (5'ATF2-URA3-3'ATF2) was demonstrated by PCR amplification on the intact cells using the aforementioned primers OTG10841 and OTG10845. Absence of APAT activity was then demonstrated in vitro according to the test described on the basis of the cell homogenate, in comparison with the parent strain which shows marked APAT activity.

The strains meeting these criteria were thus characterized as atf2 mutant strains, designated atf2-Δ::URA3. A mutant strain thus obtained starting from the parent strain FYl679 was designated TGY156 and a mutant strain obtained starting from the parent strain TGY73.4 was designated TGY158.

A sample of strain TGY156 was lodged at the Collection Nationale de Cultures de Microorganismes (CNCM) INSTITUT PASTEUR, 25, Rue du Docteur Roux 75724 PARIS CEDEX 15 FRANCE, on Feb. 2, 1998 under number I-1977.

A sample of strain TGY158 was lodged at the Collection Nationale de Cultures de Microorganismes (CNCM) INSTITUT PASTEUR, 25, Rue du Docteur Roux 75724 PARIS CEDEX 15 FRANCE, on Feb. 2, 1998 under number I-1976.

C) Stabilization of Pregnenolone in vivo in Cultures of Yeast ad Strains atf2-Δ::URA3.

Figure 6:
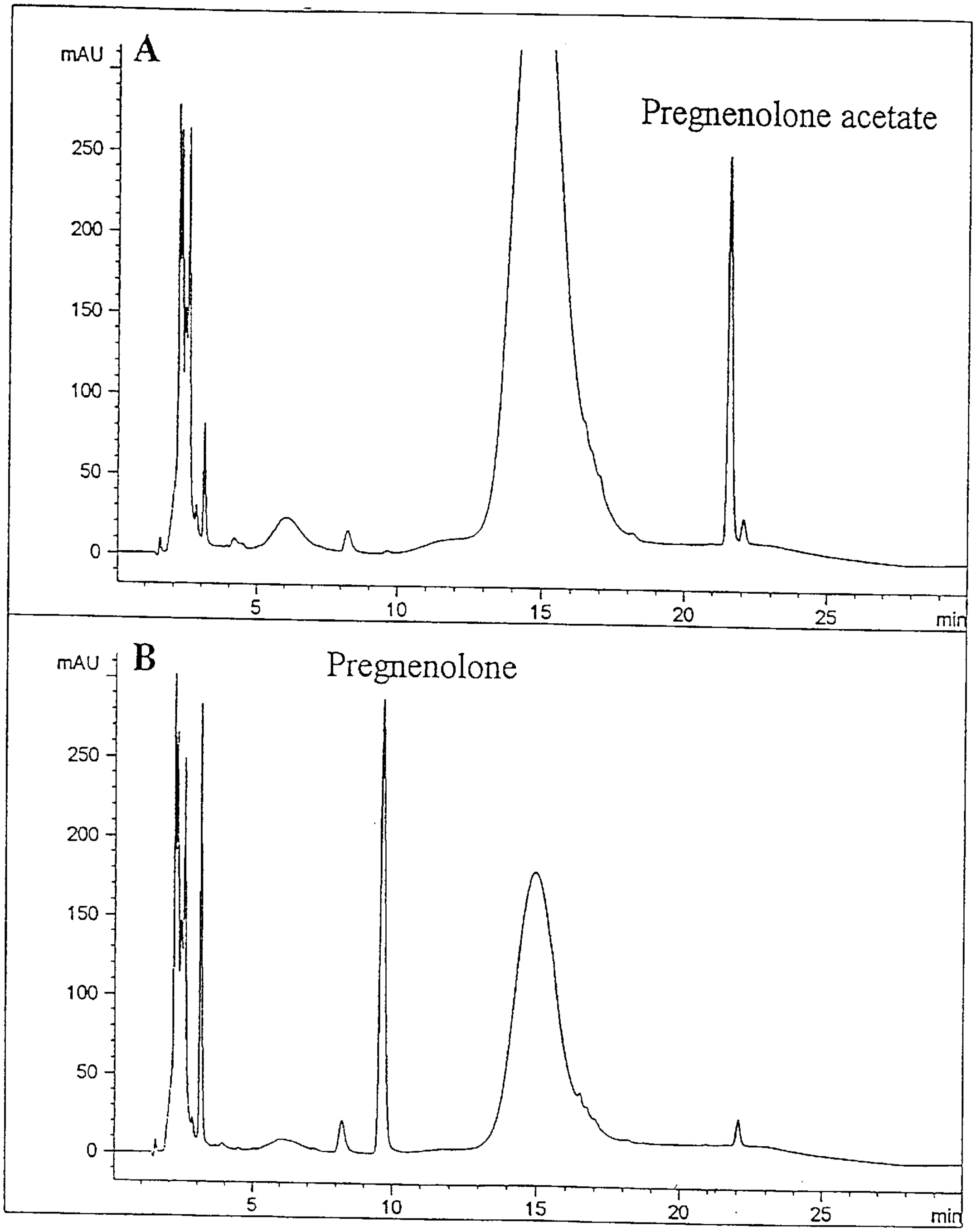
FIG. 6 shows the effect of disruption of the ATF2 gene in *S. cerevisiae* on the acetylation of pregnenolone. The presence of pregnenolone acetate is detected by RP-HPLC at 205 nm on the basis of 16-h cultures of the parent strain TGY73.4 (A) or of the mutant strain TGY158 (B).

The cells of strain TGY158 obtained above were inoculated at A600=0.1 in YPD medium (Difco) containing 100 μg/ml of pregnenolone. After 16 hours of incubation at 28° C., the steroids were extracted with dichloromethane and analysed by RP-HPLC as stated above. FIG. 6(B) shows that the mutant TGY158 has lost the ability to esterify pregnenolone whereas in the same culture conditions, the parent strain TGY73.4 converts pregnenolone to pregnenolone acetate (FIG. 6(A)).

It can be concluded on the basis of these results that the product of the ATF2 gene is responsible for esterification of pregnenolone by the yeast whereas interruption of the ATF2 gene did not lead to evident changes in cell growth in normal conditions.

EXAMPLE 3

Construction of a Yeast Strain Possessing the ATF2 Gene Disrupted by the URA3 Gene and Expressing 3β-HSD 2μ plasmids bearing a cDNA sequence coding for human 3β-HSD under the control of the CYC1 promoter of *S. cerevisiae* or of the TEF1 promoter of *S. cerevisiae* and bearing the G418 resistance gene were constructed according to the scheme in FIGS. 7A to 7C, then transformed into mutant yeast strains atf2-Δ::URA3.

Firstly, a transfer vector pTG10095, containing the cDNA sequence coding for type II human 3β-HSD described by E.

Rhèaume et al., 1991 flanked by the SalI and MluI sites and located downstream of the yeast promoter GAL10/CYC1, was generated in the following manner:

The sequence coding for 3β-HSD was subcloned by E. Rhèaume et al., 1991 as a restriction fragment SalI-NotI at the same sites of the vector Bluescript II (Stratagène). The vector obtained, described by E. Rhèaume et al., 1991 contains a NotI site located at the 3' end of the sequence coding for 3β-HSD. This vector was then digested by the NotI restriction enzyme, and treated by the Klenow fragment in the presence of DNTP in order to fill the cohesive ends, then re-ligated in the presence of the oligonucleotide possessing the following sequence:

OTG4461: CACACGCGTGTG (SEQ ID NO:7)

previously phosphorylated and hybridized on itself, so as to introduce a site MluI. The vector pTG10082 (FIG. 7A) thus obtained contains the sequence coding for 3β-HSD containing a BglII site and edged with the SalI and MluI sites, whereas the NotI site was lost. This vector still contains the natural non-coding region 5' identified by the presence of a BglII site.

In order to bring the SalI site closer to the initiator ATG upstream of which we wish to introduce the GAL10/CYC1 promoter, the vector pTG10082 was digested with the MscI restriction enzyme whose site is located in the non-coding 5' region and just upstream of the initiator ATG and by the MluI restriction enzyme. The MscI-MluI fragment, of 1.8 kb, containing the sequence coding for 3β-HSD (FIG. 7A), was isolated then ligated in the pTG10033 plasmid (E. Degryse et al., 1995) containing the GAL10/CYC1 promoter, previously digested by the SalI restriction enzyme, then digested by the MluI restriction enzyme. The pTG10095 vector (FIG. 7B) is thus obtained.

Secondly, the recombination vector pTG10268 containing the 2$\mu$ plasmid of yeast, a replicon of *E. coli*, a $CYC1_{prom}$-$PGK_{term}$ expression cassette and the selection marker LEU2 (FIG. 7B) was constructed. This vector is identical to the vector pTG10159 described (E. Degryse et al., 1995), apart from the XbaI site contained in the 2$\mu$ region which was replaced by a marker XbaI° obtained by filling of the natural site XbaI in the presence of the Klenow fragment, then by re-ligating.

The pTG10268 expression plasmid was then generated by homologous recombination by introduction of the expression block containing the promoter GAL10/CYC1p, obtained starting from the plasmid pTG10095 prepared above then digested by the NotI restriction enzyme, in the plasmid pTG10260 previously digested by the restriction enzymes SalI and MluI. The plasmid pTG10268 (FIG. 7B) contains the sequence coding for type II human 3β-HSD under the control of the promoter CYC1.

The expression plasmid pTG10862 containing the sequence coding for 3β-HSD under the control of the promoter TEF1 was then constructed in the following way (FIG. 7C):

The plasmid pTG10832 (FIG. 8) was first constructed by homologous recombination between the NotI fragment obtained from the plasmid pTG10268 prepared above, then digested by the NotI restriction enzyme and the recombination plasmid pTG10164 (E. Degryse et al., 1995) previously digested by the restriction enzymes SalI and MluI.

The expression plasmid pTG10862 was then obtained by introduction of the promoter TEF1, contained in the ClaI-SalI fragment isolated from the plasmid pTG10085 (E. Degryse et al., 1995), in place of the promoter CYC1 excised by digestion of the plasmid pTG10832 constructed above by the restriction enzymes ClaI and SalI.

The plasmid pTG10862 thus obtained (FIG. 9) and containing the cDNA sequence coding for type II human 3β-HSD was transformed respectively in the parent ,strain TGY73.4 or in its mutant atf2-Δ::URA3 corresponding to the strain TGY158 obtained in Example 2 as well as in the parent strain FYl679 or in its mutant atf2-Δ::URA3 corresponding to the strain TGY156 obtained in Example 2. The transformants were isolated as stated above on YPD medium (Difco) containing G418 at 250 $\mu$g/ml.

The candidate colonies thus obtained were then precultivated on the SD medium containing the nutritional elements necessary for each strain (histidine and uracil for strain TGY73.4; histidine for TGY158; tryptophan, histidine, leucine and uracil for strain FYl679; tryptophan, histidine and leucine for strain TGY156; each at a concentration of 100 $\mu$g/ml), then inoculated in a medium containing 100 $\mu$g/ml of pregnenolone. After 24 h of growth and bioconversion at 28° C., the steroids were extracted and measured by RP-HPLC as stated above. The results obtained, measured on 3 clones from each strain, are shown in Table 3 below:

TABLE 3

| Strain | Plasmid | Pregnenolone ($\mu$g/ml) | Progesterone ($\mu$g/ml) |
|---|---|---|---|
| TGY73.4 | pTG10862 | 1 | 0 |
| TGY15B | " | 94 | 15.2 |
| FY1679 | " | 1 | 1.3 |
| TGY156 | " | 100 | 13 |

The results show that the substrate pregnenolone is recovered almost quantitatively in the mutant strains TGY156 or TGY158 in which commencement of bioconversion of pregnenolone to progesterone is observed whereas the disappearance of pregnenolone is complete in the parent strains TGY73.4 or FYl679 which produce very little if any progesterone, but accumulate pregnenolone acetate as was shown in Example 2.

A sample of the modified strain TGY158/pTG10862 was lodged at the Collection Nationale de Cultures de Microorganismes (CNCM) INSTITUT PASTEUR, 25, Rue du Docteur Roux 75724 PARIS CEDEX 15 FRANCE, on Feb. 2, 1998 under number I-1978.

EXAMPLE 4

Construction of a Yeast Strain Possessing the ATF2 Gene Disrupted by $TEF1_{prom}$/$PGK_{term}$ (atf2-Δ::TEF1/PGK).

Strain TGY186, which is a strain derived from strain TGY156 (atf2-Δ::URA3) described in Example 2 in which the URA3 gene at the ATF2 locus has been replaced by the expression block $TEF1_{prom}$/$PGK_{term}$, was constructed as follows:

Firstly, the expression block $TEF1_{prom}$/$PGK_{term}$ was combined with the ATF2 gene by double fusion PCR following the conditions described in Example 2, but using the expression block $TEF1_{prom}$/$PGK_{term}$ of *S. cerevisiae* described by E. Degryse et al., 1995 instead of the URA3 selection marker.

The first two PCR reactions (PCR1), permitting, respectively, amplification of the 5' and 3' coding regions of the ATF2 gene flanking the insertion site of the $TEF1_{prom}$/$PGK_{term}$ block in the ATF2 disrupted target gene, were carried out using respectively, as direct and indirect primers for the 5' region, the oligonucleotides possessing the following sequences:

OTG11049: CTCTCTGTCGACATGGAAGATATAGAAGGATACGAACCAC ATATCACTC (SEQ ID NO:8) and

OTG10844: ATCAATCTCCAATTAGGCCTCTTCGGATTACCC (SEQ ID NO:9)

for the 3' region, the oligonucleotides possessing the following sequences:

OTG10846: CATTCGACATTCCCGAAGGTGACAATGACAAG. (SEQ ID NO:10)

OTG11050: AACAACACGCGTAACTATTAAAGCGACGCAAATTCGCCGATGCTTTGG (SEQ ID NO: 11)

The primers OTG11049 and OTG11050 were designated for introducing, respectively, the restriction sites SalI and MluI.

The third PCR reaction (PCR2) permitting amplification of the $TEF1_{prom}$/$PGK_{term}$ block was effected using, respectively as direct and indirect primers, the oligonucleotides possessing the following sequences:

OTG11052: GGGTAATCCGAAGAGGCCTAATTGGAGATTGATATCGATCACACAC CATAGCTTCAAAATGTTTCTAC (SEQ ID NO: 12)

OTG11053: CTTGTCATTGTCACCTTCGGGAATGTCGAATCTTCGAAACGCAGAA TTTTCGAGTTATTAAACTTAA (SEQ ID NO:13)

which introduce the restriction sites ClaI and HindIII.

Finally, combination was effected by double fusion of the PCR products obtained above, using as primers the oligonucleotides possessing the sequences OTG11049 (SEQ ID N°8) and OTG11050 (SEQ ID N°11) above, which introduce the restriction sites SalI and MluI at the ATF2 junction sites.

After purification, the final fusion product was then recombined with the ATF2 gene contained in the plasmid pTG10885 constructed as indicated below and previously digested with the restriction enzymes BstI and StuI. The plasmid pTG10888, containing the $TEF1_{prom}/PGK_{term}$ signal at the ClaI and HindIII sites edged by the flanking regions of the ATF2 gene, is thus obtained.

Preparation of the plasmid pTG10885 comprises amplification of the ATF2 gene starting from the FYl679 strain and following the conditions described in Example 2, but using, respectively as direct and indirect primers, the oligonucleotides possessing the sequences OTG11049 (SEQ ID N°8) and OTG11050 (SEQ ID N°11) above, which introduce restriction sites SalI and MluI. In the PCR product obtained, these sites were then eliminated by digestion with the restriction enzymes SalI and MluI, then treatment with the Klenow fragment of polymerase I of *E. coli*, so as to fill the sticky ends. The fragment obtained was then ligated in the expression vector pTG10031 described by E. Degryse et al., 1995 digested beforehand with enzymes ClaI and HindIII, then treated with the Klenow fragment. By transformation in *E. coli*, the plasmid pTG10885 is thus obtained, resulting from ligation of the SalI site of the PCR product, filled by using the Klenow fragment so as to obtain the sequence GTCGA with the HindIII site of the vector, filled by using the Klenow fragment so as to obtain the sequence AGCTT so as to reconstruct the HindIII site (GTCGAAGCTT) (SEQ ID NO: 14) and lose the ClaI site. The ClaI site of the vector, filled by using the Klenow fragment so as to obtain the sequence ATCG is lost after ligation to the PCR product.

The $TEF1_{prom}/PGK_{term}$ signal was then excised from plasmid pTG10888 in the form of a NotI fragment of, 1.8 kb, then was exchanged with the URA3 marker in strain TGY156 (atf2-Δ::URA3)

Strain TGY156, prepared in Example 2, used as host strain, was co-transformed with the DNA excised from plasmid pTG10888 and with the yeast vector containing an ARS origin, designated YRp7, described by Struhl et al., 1979 which makes it possible to supplement the tryptophan requirement of strain TGY156 and selective detection of colonies from their resistance to 5 fluoro-orotic acid (5-FO).

2 to 5 μg of the DNA excised from plasmid pTG10888 by digestion with the NotI restriction enzyme and from plasmid YRp7 were introduced into strain TGY156 by the lithium acetate method (Ito et al., 1983). Selection for the supplementation for a requirement for tryptophan of the strain was then effected after spreading on dishes of agar in YNGB medium (Difco) enriched with histidine and leucine (100 μg/ml of each). The candidate colonies, collected using a toothpick, were then placed on a medium containing 5-FO prepared according to Boeke et al., 1984 then the resistance to 5-FO was confirmed on the same medium, any loss of the YRp7 vector in those resistant to 5-FO being indicated by a requirement for tryptophan. Among the clones thus selected, combination of the ATF2 gene with $TEF1_{prom}$ and $PGK_{term}$ was monitored by PCR. Strain TGY186 is thus obtained.

EXAMPLE 5

Construction of a Yeast Strain Possessing the ATF2 Gene Disrupted by $TEF1_{prom}/PGK_{term}$ and Expressing $P_{450}17\alpha$.

A plasmid (pTG10435) containing a yeast replication origin ARSH4/CEN6, the URA3 selection marker and bearing a cDNA sequence coding for the bovine cytochrome $P_{450}17\alpha$ under the control of the TEF1 promoter of *S. cerevisiae* was constructed according to the scheme in FIG. 10, then transformed in a mutant yeast strain atf2-Δ::TEF1/PGK (TGY186). Firstly, a plasmid pTG10058 containing the cDNA sequence coding for the bovine cytochrome $P_{450}17\alpha$ described by Zuber et al., 1986, flanked by the SalI and MluI sites and situated downstream of the yeast promoter CYC1, was generated according to the scheme in FIG. 11: The plasmid pGB17α-5 described in patent application WO 89/10963 and containing the sequence coding for the bovine cytochrome $P_{450}17\alpha$ was opened by digestion with the XhoI restriction enzyme then treated with alkaline phosphatase.

After phosphorylation and hybridization, the oligonucleotides possessing the following sequences:

OTG4511: TCGACGGACGCGTGG (SEQ ID NO:15) and

OTG4512: TCGACCACGCGTCCG (SEQ ID NO:16)

were introduced in the XhoI site generating the plasmid pTG10104. The plasmid pTG10104 was then treated with the restriction enzymes SalI and MluI, then introduced in the plasmid pTG10031 described by E. Degryse et al., 1995 containing the yeast promoter CYC1, previously digested with the restriction enzymes SalI and MluI and treated with alkaline phosphatase. The pTG10058 vector containing the cDNA coding for the bovine cytochrome $P_{450}17\alpha$ is thus obtained (FIG. 12). The plasmid pTG10058 was then digested by the restriction enzymes SalI and MluI and treated with alkaline phosphatase. The SalI-MluI fragment of 1.7 kb containing the sequence coding for the bovine cytochrome $P_{450}17\alpha$ was isolated, then ligated in the expression vector pTG10085 described by E. Degryse et al., 1995 and containing the yeast promoter TEF1, previously digested with the enzymes SalI and MluI. The plasmid pTG 10293 (FIG. 13) in which the sequence coding for the cytochrome $P_{450}17\alpha$ is under the control of the promoter TEF1 is thus obtained.

Secondly, the expression plasmid pTG10435 was generated by homologous recombination between the recombination plasmid pTG10434 described by E. Degryse et al. 1995 and containing the sequence ARSH4/CEN6, previously digested by the enzymes SalI and MluI and the NotI fragment of 2.8 kb obtained starting from the plasmid pTG10293 prepared above.

The plasmid pTG10435 thus obtained (FIG. 14) and containing the sequence coding for the bovine cytochrome $P_{450}17\alpha$ under the control of the promoter TEF1, was then transformed respectively in the parent strain FYl679 or in strain TGY186 (atf2-Δ::TEF1/PGK) prepared in Example 4. The transformants were isolated as stated above on YNBG medium (Difco) enriched with tryptophan, histidine and leucine (100 μg/ml of each). The colonies thus obtained were then precultivated for 16 hours in YNB medium (Difco) containing 2 of glucose and 0.5% of casaminoacids, then diluted in fresh medium to A600=0.2. After 6 hours of growth, 100 μ/ml of pregnenolone or of progesterone was added. After 48 hours of growth and bioconversion at 28° C., the steroids were extracted and measured by RP-HPLC as indicated in Example 1 using, respectively, standards of pregnenolone and of 17α-hydroxypregnenolone or of progesterone and of 17α-hydroxyprogesterone.

The results obtained expressed in μg/ml are shown in Table 4 below:

TABLE 4

| Strain | FY1679/pTG10435 | TGY186/pTG10435 |
|---|---|---|
| Substrate: Pregnenolone | | |
| Pregnenolone | 0 | 67.1 |
| 17α-Hydroxypregnenolone | 0 | 42.0 |
| Substrate: Progesterone | | |
| Progesterone | 46.5 | 41.4 |
| 17α-Hydroxyprogesterone | 29.3 | 33.1 |

These results show that the capacity for bioconversion of cytochrome $P_{450}17\alpha$ expressed starting from the vector pTG10435 is nearly the same in the wild-type strain (FY) or in its mutant atf2 (TGY186) with progesterone as substrate. On the other hand, with pregnenolone as substrate, the same bioconversion is obtained in comparison with progesterone but only with the mutant atf2 (TGY186). In the wild-type strain FY, both the substrate and the product are acetylated and no free hydroxyprogesterone is detected.

A sample of the modified strain TGY186/pTG10435 was lodged at the Collection Nationale de Cultures de Microorganismes (CNCM) INSTITUT PASTEUR, 25, Rue du Docteur Roux 75724 PARIS CEDEX 15 FRANCE, on Jan. 20, 1999 under the number I-2119.

EXAMPLE 6

Construction of a Yeast Strain Possessing the ATF2 Gene Disrupted by $TEF1_{prom}/PGK_{term}$ and Co-expressing 3β-HSD and $P_{450}17\alpha$.

The plasmid pTG10417 (FIG. 21) containing the yeast replicon 2μ and two expression blocks, one coding for human 3β-HSD, the other coding for bovine cytochrome $P_{450}17\alpha$, and both under the control of the promoter CYC1 of *S. cerevisiae* and bearing the URA3-d selection marker was constructed following successively stages 1 to 3 described below (FIGS. 15A and B), then stages 4 to 6 described below, then transformed in a mutant yeast strain atf2-Δ::$TEF1_{prom}/PGK_{term}$ (TGY186)

Stage 1: Construction of the Plasmid pTG10210

The expression vector pTG10033 described by E. Degryse et al., 1995 and containing the hybrid yeast promoter GAL10/CYC1, previously digested by the restriction enzyme PvuII, was treated with alkaline phosphatase then re-ligated in the presence of the oligonucleotide that has the following sequence:

OTG1050: CCCGAATTCGGG (SEQ ID NO:17)

previously phosphorylated and hybridized on itself so as to introduce EcoRI sites at the edge of the expression block containing the promoter GAL10/CYC1. The vector pTG10210 is thus obtained.

Stage 2: Construction of the Plasmid pTG10214

The expression block containing the promoter GAL10/CYC1 present in the vector pTG10210 was then introduced in the *E. coli*-yeast shuttle vector pTG10013 described by E. Degryse et al., 1995 and containing the selection marker URA3-d.

The vector pTG10013, after digestion with the EcoRI restriction enzyme and treatment with alkaline phosphatase, was ligated in the vector pTG10210 prepared in stage 1, previously digested with the enzyme EcoRI. The vector pTG10214 thus obtained contains the expression block containing the promoter GAL10/CYC1 directed towards the 21 μreplicon.

Stage 3: Construction of the Plasmid pTG10274

In plasmid pTG10214, the promoter GAL10/CYC1 was then exchanged with the promoter CYC1 by homologous recombination after excision of the plasmid by treatment with the restriction enzymes ClaI and SalI. The expression vector pTG1031 described by E. Degryse et al., 1995 and containing the promoter CYC1 was digested by the restriction enzymes HindIII and FspI, then recombined with the plasmid pTG10214 prepared in stage 2 and previously digested with the restriction enzymes ClaI and SalI, thus generating the plasmid pTG10274 (FIG. 16).

Stage 4: Construction of the Plasmid pTG10401

Starting from the plasmid pTG10274 containing the promoter CYC1 and the plasmid pTG10293 containing the sequence coding for the cytochrome $P_{450}17\alpha$ under the control of the promoter TEF1, a new plasmid pTG10401 containing the sequence coding for the cytochrome $P_{450}17\alpha$ under the control of the promoter TEF1 was then generated by homologous recombination. The promoter CYC1 and a part of the replicon of *E. coli* were excised from the plasmid pTG10274, prepared in stage 3, by digestion with the restriction enzymes MluI and DraI. The plasmid pTG10293, prepared in Example 5, was digested with the restriction enzymes HindIII and PvuII, then recombined with the plasmid pTG10274 digested with the restriction enzymes MluI and DraI generating the plasmid pTG10401 (FIG. 17).

Stage 5: Construction of the Plasmid pTG10403

The cDNA coding for type II human 3β-HSD was then introduced in the plasmid pTG10401 under the control of the promoter CYC1. Firstly, the expression vector pTG10262 containing the cDNA coding for type II human 3β-HSD was constructed according to the scheme in FIG. 18, starting from the transfer vector pTG10095 prepared in Example 3 and the recombination vector pTG10257 containing the yeast replicon 2μ, a replicon from *E. coli*, the expression cassette of yeast $CYC1_{prom}$-$PGK_{term}$ and a URA3-d selection marker. This vector pTG10257 is identical to the recombination vector pTG10042 described by E. Degryse et al., 1995, apart from the site XbaI contained in the 2 μ region and which is replaced by a marker $XbaI_o$ obtained by filling the natural site XbaI with the Klenow fragment and then religating.

The expression block of the type II human 3β-HSD was excised from the transfer vector pTG10095 by digestion with the restriction enzyme NotI, then introduced in the recombination vector pTG10257 previously digested with the restriction enzymes SalI and MluI, generating the expression vector pTG10262 (FIG. 19). It should be noted that recombination of the block GAL10/CYC1-cDNA originating from plasmid pTG10095 in the recombination vector pTG10257 containing the promoter CYC1 produces an expression vector containing the block CYC1-cDNA.

Secondly, the expression vector pTG10262, prepared above, was digested with the restriction enzyme XmnI. The fragment obtained containing the cDNA coding for 3β-HSD was recombined with the fragment of plasmid pTG10401 prepared in stage 4 containing the cDNA coding for the cytochrome $P_{450}17\alpha$ obtained by digestion with the restriction enzyme ScaII. The plasmid pTG10403 (FIG. 20) thus obtained contains two expression blocks, one coding for 3β-HSDH under the control of the promoter CYC1, the other coding for the cytochrome $P_{450}17\alpha$ under the control of promoter TEF1.

stage 6: Construction of Plasmid pTG10417

Finally, in the above plasmid pTG10403, the promoter TEF1 was exchanged with the promoter CYC1. On the one hand, the plasmid pTG10058 described in Example 5 was digested with the restriction enzyme PvuII, which makes it possible to release a part of the sequence coding for the cytochrome $P_{450}17\alpha$ combined with the promoter CYC1 as well as most of the replicon of *E. coli*. On the other hand, part of the replicon of *E. coli* was eliminated from the plasmid pTG10403 prepared in stage 5 by digestion with the restriction enzyme DraI. By recombination-of the two plasmids previously digested in this way, the plasmid pTG10417 is finally obtained.

The plasmid pTG10417 contains the yeast replicon 2$\mu$, the URA3-d selection marker and the two expression blocks, one coding for human 3β-HSD, the other coding for the cytochrome $P_{450}17\alpha$ of bovine origin, both under the control of the yeast promoter CYC1 (FIG. 21).

The plasmid pTG10417 was then transformed respectively in the parent strain FYl679 or in strain TGY186 (atf2-α::TEF$1_{prom}$/PGK$_{term}$) prepared in Example 4. The transformants were isolated on agar-treated YNB medium (Difco), containing 0.5% of glucose, enriched with tryptophan, histidine and leucine (100 $\mu$g/ml each).

The colonies thus obtained were then precultivated for 24 hours at 28° C. in the YNB medium (Difco) containing 0.5% of glucose and 0.1% of casaminoacids, then diluted to A600=0.1 and supplemented with pregnenolone at 100 $\mu$g/ml, either in the same fresh medium (medium 1), or in the YNB medium (Difco) containing 0.1% of glucol, 2% of glycerol and 0.2% of casaminoacids (medium 2). After 48 hours of growth and bioconversion, the steroids were extracted and measured by RP-HPLC as indicated in Example 1 using the standards of pregnenolone, 17α-hydroxypregnenolone, progesterone and 17α-hydroxyprogesterone.

The results obtained, expressed in $\mu$g/ml, are shown in Table 5 (medium 1) and Table 6 (medium 2) below:

TABLE 5

| Strain | FY1679/pTG10417 | TGY166/pTG10417 |
|---|---|---|
| Pregnenolone | 0 | 58.1 |
| Pregnenolone acetate | 87.3 | 0 |
| 17α-hydroxypregnenolone | 0 | 3.1 |
| 17α-hydroxypregnenolone acetate | 0 | 0 |
| Progesterone | 10.6 | 1.4 |
| 17α-hydroxyprogesterone | 1.3 | 23.4 |

TABLE 6

| Strain | FY1679/pTG10417 | TGY156/pTG10417 |
|---|---|---|
| Pregnenolone | 0 | 54.0 |
| Pregnenolone acetate | 52.1 | 0 |
| 17α-hydroxypregnenolone | 0 | 3.4 |
| 17α-hydroxypregnenolone acetate | 12.8 | 0 |
| Progesterone | 0 | 1.4 |
| 17α-hydroxyprogesterone | 8.6 | 31.4 |

These results show that bioconversion in the wild-type strain (FY) transformed by the plasmid pTG10417 leads to accumulation of pregnenolone acetate and of 17α-hydroxypregnenolone acetate which are not transformed subsequently by the enzymes 3β-HSDH or $P_{450}17\alpha$ and that the balance of bioconversion is lower than that observed with the transformed atf2 mutant (TGY186).

A sample of the transformed strain TGY186/pTG10417 was lodged with the Collection Nationale de Cultures de Microorganismes (CNCM) INSTITUT PASTEUR, 25, Rue du Docteur Roux 75724 PARIS CEDEX 15 FRANCE, on Jan. 20, 1999 under the number I-2118.

Bibliographical References

Achstetter T., Nguyen-Juilleret M., Findeli A., Merkamm M. and Lemoine Y. (1992), Gene 110, 25–31.

Amberg D. C., Botstein D. and Beasley E. M., (1995), Yeast 11 1275–1280.

Boeke Jef D., Lacroute F. and Fink G R., (1984) Mol Gen Genet 197: 345–346.

Cauet G., Dumas B., Degryse E., Spagnoli R. and Achstetter T. (1994) in Cytochrome P-450 biochemistry, biophysics and molecular biology (Lechner M.C., ed.) pp. 583–586, John Libbey Eurotext.

Cherry J. M., Adler C., Ball C., Dwight S., Chervitz S., Jia Y., Juvik G., Roe T., Weng S. and Botstein D., "Saccharomyces Genome Database" http://genome-www.stanford.edu/Saccharomyces/

Degryse E., J. Biotech. 39 (1995) 181–187.

Degryse E., Dumas B., Dietrich M., Laruelle L. and Achstetter T. (1995). Yeast 11: 629–640.

Degryse E. (1996), Gene 170, 45–50.

Dumas B., Cauet G., Degryse E., Spagnoli R. & Achtetter T. (1994). Cytochrome P450.8$^{th}$ International Conference. Ed. M. C. Lechner. John Libbey Eurotext, Paris pp. 527–530.

Fiechter A., Fuhrmann G.F. and Käppeli O., (1981). Adv. Microb. Physiol. 22, 123–183.

Fujii T., Nagasawa N., Iwamatsu A., Bogaki T., Tamai Y. and Hamachi M. (1994) Appl. Environ. Microbiol. 60, 2786–2792.

Hanahan D., J. Mol. Biol. 166 (1983) 557–580.

Hubacek J. and Glover S. W., (1970), J. Mol., Biol. 50: 111–127.

Ito H., Fukuda Y., Murata K. and Kimura A., 1983, Journal of Bacteriology, 163–168.

Rhèaume E., Lachance Y., Zhao H. -F., Breton N., Dumont M., de Launoit Y., Trudel C., Luu-The V., Simard J. & Labrie F. (1991). Mol. Endocrinol. 5, 1147–1157.

Rose M., Grisafi P. and Botstein D., Gene 29, 113–124 (1984).

Rosenfeld J., Capdevielle J., Guillemot J. C. and Ferrara P. (1992) Anal. Biochem. 203, 173–179.

Sambrook J., Fritsch E. F. and Maniatis T., (1989). Molecular Cloning: A Laboratory Manual. Cold Spring Harbor University Press, 2nd edition, Cold Spring Harbor.

Sherman F. (1991) Methods in Enzymology 194, 3–21.

Simard J., Durocher F., Mèbarki F., Turgeon C., Sanchez R., Labrie Y., Couet J., Trudel C., Rhèaume E., Morel Y., Luu-The V. And Labrie F. (1996) J. Endocrinol. 150, 5189–5207

Struhl K., Stinchomb D T., Scherer S. and Davis R W., 1979, Proc. Natl. Acad. Sci. USA Vol. 76, N°3, 1035–1039.

Thierry A., Fairhead C. and Dujon B., Yeast; Vol. 6: 521–534 (1990).

Zuber M X., Simpson E R. and Waterman M R.,(1986a) Science 234, 1258–1261.

What is claimed is:

1. A modified yeast strain wherein acetyl-CoA pregnenolone acetyltransferase (APAT) activity has been eliminated by altering the gene ATF2 of *Saccharomyces cerevisiae* or a homolog of gene ATF2 which codes for this activity, by insertion, deletion or substitution of a DNA sequence in the functional elements of said gene, resulting in stabilization of 3β-hydroxysteroids.

* * * * *

SEQUENCE LISTING

```
<160> NUMBER OF SEQ ID NOS: 20

<210> SEQ ID NO 1
<211> LENGTH: 50
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 1

aaaagtcgac aaaatggaag atatagaagg atacgaacca catatcactc                50


<210> SEQ ID NO 2
<211> LENGTH: 33
<212> TYPE: DNA
<213> ORGANISM: ARTIFICIAL SEQUENCE
<220> FEATURE:
<221> NAME/KEY: misc_feature
<222> LOCATION: Complement((1)..(33))
<223> OTHER INFORMATION: OLIGONUCLEOTIDE

<400> SEQUENCE: 2

atcaatctcc aattaggcct cttcggatta ccc                                  33


<210> SEQ ID NO 3
<211> LENGTH: 32
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 3

cattcgacat tcccgaaggt gacaatgaca ag                                   32


<210> SEQ ID NO 4
<211> LENGTH: 46
<212> TYPE: DNA
<213> ORGANISM: ARTIFICIAL SEQUENCE
<220> FEATURE:
<221> NAME/KEY: misc_feature
<222> LOCATION: Complement((1)..(46))
<223> OTHER INFORMATION: OLIGONUCLEOTIDE

<400> SEQUENCE: 4

aaaaacgcgt aactattaaa gcgacgcaaa ttcgccgatg gtttgg                    46


<210> SEQ ID NO 5
<211> LENGTH: 79
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 5

gggtaatccg aagaggccta attggagatt gataagcttt tcaattcaat tcatcatttt     60

ttttttattc ttttttttg                                                  79


<210> SEQ ID NO 6
<211> LENGTH: 63
<212> TYPE: DNA
<213> ORGANISM: ARTIFICIAL SEQUENCE
<220> FEATURE:
<221> NAME/KEY: misc_feature
<222> LOCATION: Complement((1)..(63))
<223> OTHER INFORMATION: OLIGONUCLEOTIDE
```

-continued

<400> SEQUENCE: 6
cttgtcattg tcaccttcgg gaatgtcgaa tggggtaata actgatataa ttaaattgaa 60
ctc 63

<210> SEQ ID NO 7
<211> LENGTH: 12
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 7
cacacgcgtg tg 12

<210> SEQ ID NO 8
<211> LENGTH: 49
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 8
ctctctgtcg acatggaaga tatagaagga tacgaaccac atatcactc 49

<210> SEQ ID NO 9
<211> LENGTH: 33
<212> TYPE: DNA
<213> ORGANISM: ARTIFICIAL SEQUENCE
<220> FEATURE:
<221> NAME/KEY: misc_feature
<222> LOCATION: Complement((1)..(33))
<223> OTHER INFORMATION: OLIGONUCLEOTIDE

<400> SEQUENCE: 9
atcaatctcc aattaggcct cttcggatta ccc 33

<210> SEQ ID NO 10
<211> LENGTH: 32
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 10
cattcgacat tcccgaaggt gacaatgaca ag 32

<210> SEQ ID NO 11
<211> LENGTH: 48
<212> TYPE: DNA
<213> ORGANISM: ARTIFICIAL SEQUENCE
<220> FEATURE:
<221> NAME/KEY: misc_feature
<222> LOCATION: Complement((1)..(48))
<223> OTHER INFORMATION: OLIGONUCLEOTIDE

<400> SEQUENCE: 11
aacaacacgc gtaactatta aagcgacgca aattcgccga tgctttgg 48

<210> SEQ ID NO 12
<211> LENGTH: 68
<212> TYPE: DNA
<213> ORGANISM: ARTIFICIAL SEQUENCE
<220> FEATURE:
<223> OTHER INFORMATION: OLIGONUCLEOTIDE

-continued

<400> SEQUENCE: 12
gggtaatccg aagaggccta attggagatt gatatcgatc acacaccata gcttcaaaat 60
gtttctac 68

<210> SEQ ID NO 13
<211> LENGTH: 67
<212> TYPE: DNA
<213> ORGANISM: ARTIFICIAL SEQUENCE
<220> FEATURE:
<221> NAME/KEY: misc_feature
<222> LOCATION: Complement((1)..(67))
<223> OTHER INFORMATION: OLIGONUCLEOTIDE

<400> SEQUENCE: 13
cttgtcattg tcaccttcgg gaatgtcgaa tcttcgaaac gcagaatttt cgagttatta 60
aacttaa 67

<210> SEQ ID NO 14
<211> LENGTH: 10
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 14
gtcgaagctt 10

<210> SEQ ID NO 15
<211> LENGTH: 15
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 15
tcgacggacg cgtgg 15

<210> SEQ ID NO 16
<211> LENGTH: 15
<212> TYPE: DNA
<213> ORGANISM: ARTIFICIAL SEQUENCE
<220> FEATURE:
<221> NAME/KEY: misc_feature
<222> LOCATION: Complement((1)..(15))
<223> OTHER INFORMATION: OLIGONUCLEOTIDE

<400> SEQUENCE: 16
tcgaccacgc gtccg 15

<210> SEQ ID NO 17
<211> LENGTH: 12
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 17
cccgaattcg gg 12

<210> SEQ ID NO 18
<211> LENGTH: 10
<212> TYPE: PRT
<213> ORGANISM: Saccharomyces cerevisiae

<400> SEQUENCE: 18

-continued

```
Ile Ser Glu Gln Phe Lys Lys Asp Asp Phe
  1               5                  10


<210> SEQ ID NO 19
<211> LENGTH: 16
<212> TYPE: PRT
<213> ORGANISM: Saccharomyces cerevisiae

<400> SEQUENCE: 19

Leu Ile Glu Leu Ile Ser Pro Val Ile Ile Pro Leu Gly Asn Pro Lys
  1               5                  10                  15


<210> SEQ ID NO 20
<211> LENGTH: 535
<212> TYPE: PRT
<213> ORGANISM: Saccharomyces cerevisiae

<400> SEQUENCE: 20

Met Glu Asp Ile Glu Gly Tyr Glu Pro His Ile Thr Gln Glu Leu Ile
  1               5                  10                  15

Asp Arg Gly His Ala Arg Arg Met Gly His Leu Glu Asn Tyr Phe Ala
             20                  25                  30

Val Leu Ser Arg Gln Lys Met Tyr Ser Asn Phe Thr Val Tyr Ala Glu
         35                  40                  45

Leu Asn Lys Gly Val Asn Lys Arg Gln Leu Met Leu Val Leu Lys Val
     50                  55                  60

Leu Leu Gln Lys Tyr Ser Thr Leu Ala His Thr Ile Ile Pro Lys His
 65                  70                  75                  80

Tyr Pro His His Glu Ala Tyr Tyr Ser Ser Glu Glu Tyr Leu Ser Lys
                 85                  90                  95

Pro Phe Pro Gln His Asp Phe Ile Lys Val Ile Ser His Leu Glu Phe
            100                 105                 110

Asp Asp Leu Ile Met Asn Asn Gln Pro Glu Tyr Arg Glu Val Met Glu
        115                 120                 125

Lys Ile Ser Glu Gln Phe Lys Lys Asp Asp Phe Lys Val Thr Asn Arg
    130                 135                 140

Leu Ile Glu Leu Ile Ser Pro Val Ile Ile Pro Leu Gly Asn Pro Lys
145                 150                 155                 160

Arg Pro Asn Trp Arg Leu Ile Cys Leu Pro Gly Lys Asp Thr Asp Gly
                165                 170                 175

Phe Glu Thr Trp Lys Asn Phe Val Tyr Val Thr Asn His Cys Gly Ser
            180                 185                 190

Asp Gly Val Ser Gly Ser Asn Phe Phe Lys Asp Leu Ala Leu Leu Phe
        195                 200                 205

Cys Lys Ile Glu Glu Lys Gly Phe Asp Tyr Asp Glu Glu Phe Ile Glu
    210                 215                 220

Asp Gln Val Ile Ile Asp Tyr Asp Arg Asp Tyr Thr Glu Ile Ser Lys
225                 230                 235                 240

Leu Pro Lys Pro Ile Thr Asp Arg Ile Asp Tyr Lys Pro Ala Leu Thr
                245                 250                 255

Ser Leu Pro Lys Phe Phe Leu Thr Thr Phe Ile Tyr Glu His Cys Asn
            260                 265                 270

Phe Lys Thr Ser Ser Glu Ser Thr Leu Thr Ala Arg Tyr Ser Pro Ser
        275                 280                 285

Ser Asn Ala Asn Ala Ser Tyr Asn Tyr Leu Leu His Phe Ser Thr Lys
    290                 295                 300
```

-continued

```
Gln Val Glu Gln Ile Arg Ala Gln Ile Lys Lys Asn Val His Asp Gly
305                 310                 315                 320

Cys Thr Leu Thr Pro Phe Ile Gln Ala Cys Phe Leu Val Ala Leu Tyr
                325                 330                 335

Arg Leu Asp Lys Leu Phe Thr Lys Ser Leu Leu Glu Tyr Gly Phe Asp
            340                 345                 350

Val Ala Ile Pro Ser Asn Ala Arg Arg Phe Leu Pro Asn Asp Glu Glu
        355                 360                 365

Leu Arg Asp Ser Tyr Lys Tyr Gly Ser Asn Val Gly Gly Ser His Tyr
    370                 375                 380

Ala Tyr Leu Ile Ser Ser Phe Asp Ile Pro Glu Gly Asp Asn Asp Lys
385                 390                 395                 400

Phe Trp Ser Leu Val Glu Tyr Tyr Tyr Asp Arg Phe Leu Glu Ser Tyr
                405                 410                 415

Asp Asn Gly Asp His Leu Ile Gly Leu Gly Val Leu Gln Leu Asp Phe
            420                 425                 430

Ile Val Glu Asn Lys Asn Ile Asp Ser Leu Leu Ala Asn Ser Tyr Leu
        435                 440                 445

His Gln Gln Arg Gly Gly Ala Ile Ile Ser Asn Thr Gly Leu Val Ser
    450                 455                 460

Gln Asp Thr Thr Lys Pro Tyr Tyr Val Arg Asp Leu Ile Phe Ser Gln
465                 470                 475                 480

Ser Ala Gly Ala Leu Arg Phe Ala Phe Gly Leu Asn Val Cys Ser Thr
                485                 490                 495

Asn Val Asn Gly Met Asn Met Asp Met Ser Val Val Gln Gly Thr Leu
            500                 505                 510

Arg Asp Arg Gly Glu Trp Glu Ser Phe Cys Lys Leu Phe Tyr Gln Thr
        515                 520                 525

Ile Gly Glu Phe Ala Ser Leu
    530                 535
```